United States Patent [19]
Ullrich et al.

[11] Patent Number: 5,861,266
[45] Date of Patent: Jan. 19, 1999

[54] TREATMENT OF DIABETES MELLITUS AND INSULIN RECEPTOR SIGNAL TRANSDUCTION

[75] Inventors: Axel Ullrich; Reiner Lammers; Alexei Igorevich Kharitonenkov, all of München, Germany; Jan M. Sap; Joseph Schlessinger, both of New York, N.Y.

[73] Assignees: New York University, New York, N.Y.; Max-Planck-Gesellschaft zur Forderung der Wissenshaften e.V., Munich, Germany

[21] Appl. No.: 203,189

[22] Filed: Feb. 28, 1994

[51] Int. Cl.$^6$ .............................. C12Q 1/42; C12N 9/99; A61K 39/395; A61K 35/78

[52] U.S. Cl. ................. 435/21; 435/18.4; 424/130.1; 424/195.1; 514/2; 514/866

[58] Field of Search .................. 435/21, 184; 514/2, 514/866; 424/130.1, 195.1

[56] References Cited

U.S. PATENT DOCUMENTS 5,155,031  10/1992  Posner et al. ........................... 435/184

FOREIGN PATENT DOCUMENTS

WO 92/01050  1/1992  WIPO.
WO 92/13083  8/1992  WIPO.
WO 94/01119  1/1994  WIPO.
WO 94/08600  4/1994  WIPO.

OTHER PUBLICATIONS

Goldstein et al., 1993, "Regulation of Insulin Receptor Signaling by Protein–Tyrosine Dephosphorylation," *Receptor 3*: (1) 1–15.

Mcguire et al., 1991, "Abnormal Regulation of Protein Tyrosine Phosphatase Activities in Skeletal Muscle in Insulin–Resistant Humans," *Diabetes 40*: 938–942.

Meyerovitch et al., 1989, "Hepatic Phosphotyrosine Phosphatase Activity and Its Alterations in Diabetic Rats," *J. Clin. Invest. 84*: 976–983.

Fantus et al., 1990, "Vanadate Augments Insulin Binding and Prolongs Insulin Action in Rat Adipocytes," *Endocrinol. 127*: 2716–2725.

Shechter, Y., 1990, "Insulin–Mimetic Effects of Vanadate," *Diabetes 39*: 1–5.

Matthews et al., 1992, Characterization of hematopoietic intracellular protein tyrosine phosphatases:Description of a phosphatase containing an SH2 domain and another enriched in proline–, glutamic acid–, serine–, and threonine–rich sequences, Mol. Cell. Biol. 12:2396–2405.

Gu et al., 1991, Identification, cloning, and expression of a cytosolic megakaryocyte protein–tyrosine–phosphatase with sequence homology to cytoskeletal protein 4.1, Proc. Natl. Acad. Sci. USA 88:5867–5871.

Tsai et al., 1991, Isolation and characterization of temperature–sensitive and thermostable mutants of the human receptor–like protein tyrosine phosphatase LAR, J. Biol. Chem. 266(16):10534–10543.

Krueger et al., 1990, Structural diversity and evolution of human receptor–like protein tyrosine phosphatases, EMBO J. 9:3241–3252.

Sap et al., 1990, Cloning and expression of a widely expressed receptor tyrosine phosphatase, Proc. Nat. Acad. Sci. USA 87:6112–6116.

Streuli et al., 1990, Distinct functional roles of the two intracellular phosphatase like domains of the receptor–linked protein tyrosine phosphatases LCA and LAR, EMBO Journal 9:2399–2407.

Tonks et al., 1990, CD45, an integral membrane protein tyrosine phosphatase, J. Biol. Chem. 265:10674–10680.

Cool et al., 1989, CDNA isolated from a human T–cell library encodes a member of the protein–tyrosine–phosphatase family, Proc. Natl. Acad. Sci. USA 86:5257–5261.

Pallen et al., 1988, Purification of a phosphotyrosine phosphatase that dephosphorylates the epidermal growth factor receptor autophosphorylation sites, Ann N.Y. Acad. Sci. 51:299–308.

Zhang and Roth, 1992, The insulin receptor–related receptor, J. Biol. Chem. 267(26):18320–18328.

Nissley et al., 1991, Insulin–like growth factor receptors, Growth Factors 5:29–43.

Soos et al., 1986, Monoclonal antibodies reacting with multiple epitopes on the human insulin receptor, Biochem. J. 235:199–208.

Ullrich et al., 1986, Insulin–like growth factor I primary structure: comparison with insulin receptor suggests structural determinants that define functional specificity, EMBO J. 5:2503–2512.

Ullrich et al., 1985, Human insulin receptor and its relationship to the tyrosine kinase family of oncogenes, Nature 313:756–761.

den Hertog et al., 1993, Receptor protein tyrosine phosphatase α activates $pp60^{c-src}$ and is involved in neuronal differentiation, EMBO J. 12(10):3789–3798.

Fantl et al., 1993, Signalling by receptor tyrosine kinases, Ann. Rev. Biochem. 62:453–481.

Lammers et al., 1993, Differential activities of protein tyrosine phosphatases in intact cells, J. Biol. Chem. 268(30):22456–22462.

(List continued on next page.)

*Primary Examiner*—John W. Rollins
*Attorney, Agent, or Firm*—Pennie & Edmonds LLP

[57] ABSTRACT

The present invention relates to novel modalities of treatment of diabetes, and other diseases caused by dysfunctional signal transduction by insulin receptor type tyrosine kinases (IR-PTK). Applicants discovered that IR-PTK activity may be modified by modulating the activity of a tyrosine phosphatase, and IR-PTK signal transduction may be triggered even in the absence of ligand. Methods for identifying compounds that, by modulating RPTPα or RPTPε activity, elicit or modulate insulin receptor signal transduction are also described.

26 Claims, 11 Drawing Sheets

OTHER PUBLICATIONS

Faure et al., 1992, The dephosphorylation of insulin and epidermal growth factor receptors; role of endosome–associated phosphotyrosine phosphatase(s), J. Biol. Chem. 267(16):11215–11221.

Goldstein et al., 1992, Protein–tyrosine phosphatases and the regulation of insulin action, J. Cell Biol. 48:33–42.

Schlessinger and Ullrich, 1992, Growth factor signaling by receptor tyrosine kinases, Neuron 9:383–391.

Zheng et al., 1992 Cell transformation and activation of $pp60^{c-src}$ by overexpression of a protein tyrosine phosphatase, Nature 359:336–339.

Sun et al., 1991, Structure of the insulin receptor substrate IRS–1 defines a unique signal transduction protein, Nature 352:73–77.

Lammers et al., 1990, Transphosphorylation as a possible mechanism for insulin and epidermal growth factor receptor activation, J. Biol. Chem. 265(28):16886–16890.

Ostergaard et al., 1989, Expression of CD45 alters phosphorylation of the lck–encoded tyrosine protein kinase in murine lymphoma T–cell lines, Proc. Natl. Acad. Sci. USA 86:8959–8963.

Mustelin et al., 1989, Rapid activation of the T–cell tyrosine protein kinase pp56lck by the CD45 phosphotyrosine phosphatase, Proc. Natl. Acad. Sci. USA 86:6302–6306.

Schlessinger et al., 1988 Signal Transduction by allosteric receptor oligomerization, Trends in Biochemical Sciences 13:443–447.

Machicao et al., 1982, Phosphorylation–dephosphorylation of purified insulin receptor from human placenta; effect of insulin, FEBS Letters 149(1):96–100.

Fantus et al., 1989, Pervanadate [Peroxide(s) of vanadate] mimics insulin action in rat adipocytes via activation of the insulin receptor tyrosine kinase, Biochem. 28:8864–8871.

Kadota et al., 1987, Stimulation of Insulin–like growth factor II receptor binding and insulin receptor kinase activity in rat adipocytes, J. Biol. Chem. 262(17):8252–8256.

Meyerovitch et al., 1987, Oral administration of vanadate normalizes blood glucose levels in streptozotocin–treated rats, J. Biol. Chem. 262(14):6658–6662.

Swarup et al., 1982, Inhibition of membrane phosphotyrosyl–protein phosphatase activity by vanadate, Biochem. Biophys. Res. Comm. 107(3):1104–1109.

Tamura et al., 1984, A novel mechanism for the insulin–like effect of vanadate on glycogen synthase in rat adipocytes, J. Biol. Chem. 259(10):6650–6658.

Walton and Dixon, 1993, Protein tyrosine phosphatases, Ann. Rev. Biochem. 62:101–120.

Pot and Dixon, 1992, A thousand and two protein tyrosine phosphatases, Biochem. Biophys. Acta 1136:35–43.

Taylor et al., 1992, Structural framework for the protein kinase family, Ann. Rev. Cell Biol. 8:429–462.

Ullrich and Schlessinger, 1990, Signal transduction by receptors with tyrosine kinase activity, Cell 61:203–212.

Hunter, 1989, Protein–tyrosine phosphatases: The other side of the coin, Cell 58:1013–1016.

Yarden and Ullrich, 1988, Growth factor receptor tyrosine kinases, Ann. Rev. Biochem. 57:443–478.

TREATMENT OF DIABETES MELLITUS AND INSULIN RECEPTOR SIGNAL TRANSDUCTION

1. INTRODUCTION

The present invention relates to novel modalities for treatment of diabetes, and other diseases caused by dysfunctional signal transduction by receptor type tyrosine kinases, in particular the insulin receptor.

The present invention further relates to methods for screening and identifying compounds capable of modulating the activity of phosphotyrosine phosphatases that regulate insulin receptor signal transduction. Such compounds may be used in the treatment of diabetes and other diseases mediated by the insulin receptor type tyrosine kinases.

2. BACKGROUND OF THE INVENTION

2.1. SIGNAL TRANSDUCTION

Cellular signal transduction is a fundamental mechanism whereby external stimuli that regulate diverse cellular processes are relayed to the interior of cells. The process is generally initiated by the binding of extracellular factors (such as hormones and growth factors) to membrane receptors on the cell surface. The biochemical pathways through which signals are transmitted within cells comprise a circuitry of directly or functionally connected interactive proteins. Each protein component in a pathway integrates signals from upstream activators and passes them onto various downstream effector proteins.

One of the key biochemical mechanisms of signal transduction involves the reversible phosphorylation of tyrosine residues on proteins. The phosphorylation state of a protein may affect its conformation and/or enzymatic activity as well as its cellular location. The phosphorylation state of a protein is modified through the reciprocal actions of protein tyrosine kinases (PTKs) and protein tyrosine phosphatases (PTPs). Generally, the level of tyrosine phosphorylation increases after the cell has been stimulated by an extracellular factor. Research in this area has largely focused on protein tyrosine kinases (Sefton et al., 1980 Cell 20:807–16; Heldin & Westermark, 1984 Cell 37:9–20; Yarden and Ullrich, 1988 Ann. Rev. Biochem. 57:443–78; Ullrich and Schlessinger, 1990 Cell, 61:203–12).

Protein tyrosine kinases comprise a large family of transmembrane as well as cytoplasmic enzymes with multiple functional domains (Taylor et al., 1992 Ann. Rev. Cell Biol. 8:429–62). The binding of an extracellular factor or ligand allosterically transduces a signal to the inner face of the cell membrane where the cytoplasmic portion of the receptor protein tyrosine kinase (RPTKs) initiates a cascade of molecular interactions that disseminate the signal throughout the cell and into the nucleus.

Ligand-induced activation of the kinase domain and its signalling potential are mediated by receptor dimerization. Receptor dimerization stabilizes the interactions between adjacent cytoplasmic domains, and activates the intrinsic kinase activity of the receptor. Once activated, the receptor self-phosphorylates (autophosphorylation or transphosphorylation) on specific tyrosine residues in the cytoplasmic domain (Schlessinger, 1988, Trends Biochem. Sci. 13:443–7, Schlessinger and Ullrich, 1992, Neuron, 9:383–91, and references therein). In case of insulin receptor-type RPTKs, the receptor exists naturally as a dimer, undergoing a conformational change and autophosphorylation upon ligand binding.

While it is widely appreciated that these RPTKs assume a key role in signal transduction, the part played by phosphatases remains poorly understood. Like the PTKs, the protein tyrosine phosphatases comprise a family of transmembrane and cytoplasmic enzymes. (Hunter, 1989, Cell 58:1013–16; Fischer et al., 1991, Science 253:401–6; Saito & Streuli, 1991, Cell Growth and Differentiation 2:59–65; Pot and Dixon, 1992, Biochem. Biophys. Acta, 1136:35–43). It is believed that RPTKs play a triggering role in signal transduction, while RPTPs guarantee that the trigger is reset, thereby serving to deactivate the pathway. However, certain kinases may provide inhibitory functions by phosphorylation of inhibitor sites on a signaling molecule, and certain phosphatases may have triggering functions by dephosphorylating the inhibitory sites. The first PTP purified was a cytoplasmic (nonreceptor) PTP (CPTP), PTP1B (Tonks et al., 1988, J. Biol. Chem. 263:6722–30) which unexpectedly shared sequence similarity with the cytoplasmic domain of a leucocyte surface antigen, CD45. Subsequently, CD45 was shown to possess tyrosine phosphatase activity and was recognized as a receptor-type PTP (RPTP) (Tonks et al., 1988 Biochemistry 27:8696–701).

While mammalian RPTPs and CPTPs share a homologous core catalytic domain, diverse noncatalytic sequences have also been observed. Some RPTPs contain Ig-like and/or fibronectin type III repeats in their extracellular portions (e.g., LAR, Streuli et al., 1988, J. Exp. Med. 168:1523), others have small extracellular glycosylated segments (e.g., RPTPα, Sap et al., 1990, Proc. Natl. Acad. Sci. USA 87:6112; and RPTPε, Krueger et al., 1990, EMBO J 9:3241). In all cases, the putative ligands have yet to be identified. Other phosphotyrosine phosphatases such as PTP1B, PTPμ, PTP1C, TC-PTP, PTPH1, RPTPκ, and CD45 have been cloned and their cDNAs are described in Chernoff et al., 1990, Proc. Natl. Acad. Sci. USA, 87:2735–9; Gebbink et al., 1991, FEBS Lett. 290:123–30; Shen et al., 1991, Nature, 352:736–9; Cool et al., 1989, Proc. Natl. Acad. Sci. USA., 86:5257–61; Gu et al., 1991, Proc. Natl. Acad. Sci. USA, 88:5867–71; Jiang et al., 1993, Mol. Cell Biol., 13:2942–51 and; Charbonneau et al., 1988, Proc. Natl. Acad. Sci. USA, 85:7182–6 respectively. Some PTPs and PTKs contain similar structural components. For example, members of both protein families may contain a homologous SH2 (src-homology 2) domain (reviewed in Koch et al., 1991, Science 252:668–74).

Although PTPs appear to be an integral part of the signal transduction mechanism, their specific functions have not been defined (Walton et al., 1993, Ann. Rev. Biochem. 62: 101–120).

2.2. THE INSULIN RECEPTOR

The insulin receptor (IR)(Ullrich et al., 1985, Nature 313:756–61) is the prototype for a family of RPTKs structurally defined as a heterotetrameric species of two α and two β subunits. Other members of the insulin receptor-type protein tyrosine kinase (IR-PTK) family include the receptor for insulin-like growth factor I (IGF-1 R; Ullrich et al., 1986, EMBO J 5:2503–12) and the insulin related receptor (IRR; Zhang et al., 1992, J. Biol. Chem. 267:18320–8), the ligand (s) for which are at present unknown.

Insulin binding to the insulin receptor triggers a variety of metabolic and growth promoting effects. Metabolic effects include glucose transport, biosynthesis of glycogen and fats, inhibition of triglyceride breakdown, and growth promoting effects include DNA synthesis, cell division and differentiation. It is known that some of these biological effects of insulin can be mimicked by vanadium salts such as vanadates and pervanadates. However, this class of compounds appears to inhibit phosphotyrosine phosphatases generally, and are potentially toxic because they contain heavy metal (U.S. Pat. No. 5,155,031; Fantus et al., 1989, Biochem., 28:8864–71; Swarup et al., 1982, Biochem. Biophys. Res. Commun. 107:1104–9).

2.3. DIABETES MELLITUS

Diabetes mellitus is a heterogeneous primary disorder of carbohydrate metabolism with multiple etiologic factors that generally involve insulin deficiency or insulin resistance or both. Type I, or juvenile onset, or insulin-dependent diabetes mellitus, is present in patients with little or no endogenous insulin secretory capacity. These patients develop extreme hyperglycemia and are entirely dependent on exogenous insulin therapy for immediate survival. Type II, or adult onset, or non-insulin-dependent diabetes mellitus, occurs in patients who retain some endogenous insulin secretory capacity, however the great majority of them are both insulin deficient and insulin resistant. Insulin resistance can be due to insufficient insulin receptor expression, reduced insulin-binding affinity, or any abnormality at any step along the insulin signaling pathway. (Olefsky, 1988, in "Cecil Textbook of Medicine," 18th Ed., 2:1360–81) Overall, in the United States the prevalence of diabetes is probably between 2 and 4 percent, with Type I comprising 7 to 10 percent of all cases. Secondary complications of diabetes have serious clinical implications. Approximately 25 percent of all new cases of end-stage renal failure occur in patients with diabetes. About 20,000 amputations (primarily of toes, feet, and legs) are carried out in patients with diabetes, representing approximately half of the nontraumatic amputations performed in the United States. Furthermore, diabetes is the leading cause of new cases of blindness, with approximately 5000 new cases occurring each year.

Insulin is the primary mode of therapy in all patients with Type I and in many with Type II diabetes. Depending on the number of injections per day and type(s) of insulin used, the regimen can be more or less intensive. The most intensive method consists of constant insulin delivery into a subcutaneous site in the abdominal wall via an open loop delivery device consisting of a small insulin pump that must be worn by the patient essentially 24 hours a day. Oral hypoglycemic agents such as sulfonylureas are effective in Type II patients but approximately 10 to 20 percent of patients do not respond or cease to respond 12–24 months after beginning treatment.

Effective control of glucose level is difficult to achieve for prolonged periods even with the most meticulous mode of insulin therapy in the most motivated patients. Transplantation of the pancreas or islet cells, which normally produce insulin, continues to receive extensive study as a potential treatment. In addition, efforts towards developing newer and better external or implantable insulin-delivery devices integrated with a glucose sensor continues.

3. SUMMARY OF THE INVENTION

The present invention relates to novel modalities for treatment of diabetes, and other diseases caused by dysfunctional signal transduction by the insulin receptor (IR) class of protein tyrosine kinases. The present invention further relates to methods for screening and identifying compounds which modulate the activity of the IR-associated protein tyrosine phosphatases, and thus have uses in the treatment of diabetes and other diseases.

The invention is based, in part, on the Applicants' discovery that certain PTP's, in particular, RPTPα and RPTPε, specifically regulate the insulin receptor signalling pathway. The novel modalities for treatment of insulin-related disorders, such as diabetes mellitus described herein, are based on modulating the phosphatase activities that are specifically associated with the insulin receptor activity. Modulation of the PTP activity can be accomplished in a variety of ways including but not limited to the use of compounds or drugs that inhibit or enhance the PTP activity, antisense or ribozyme approaches that "knock out" the PTP activity, or gene therapy approaches to correct defects in the PTP or restore the regulated expression of the PTP. The invention is also based, in part, on the Applicants' discovery of certain compounds that specifically modulate the activity of the controlling RPTP, thereby prolonging or enhancing signal transduction mediated by the insulin receptor. Such compounds should demonstrate low toxicity since they are specific for the PTPs associated with insulin receptor activity, and do not significantly affect the activity of other PTPs that are non-specific. Therefore, compounds which demonstrate specificity for the PTPs associated with insulin receptor activity are preferred for use in the therapeutic methods of the invention.

In another embodiment of the invention, applicants have developed cell lines genetically engineered to coexpress IR and RPTPα or RPTPε, and methods to identify compounds that specifically elicit or modulate insulin receptor signal transduction.

4. BRIEF DESCRIPTION OF THE FIGURES

FIG. 1 shows the differential effects of PTPs on the phosphotyrosine content of transiently coexpressed IR type RTKS. Total cell lysate of cells transfected with the indicated DNA were separated by SDS-PAGE and transferred to a filter which was probed with an anti-phosphotyrosine ($\alpha$-PY) antibody. Lanes from left to right: IR alone, IR+TC-PTP, IR+RPTPα, IR+RPTPε, IR+TC-PTP mutant, IGF-1 R alone, IGF-1 R+TC-PTP, IGF-1 R+RPTPα, IGF-1 R+RPTPε, IGF-1 R +TC-PTP mutant.

FIG. 2 shows the differential effects of a panel of PTPs on the phosphotyrosine content of the coexpressed IR precursor and β subunit, and IRS-1 in the presence and absence of insulin as indicated. Total cell lysate of cells transfected with the indicated DNA were separated by SDS-PAGE and transferred to a filter which was probed with an anti-phosphotyrosine antibody. Lane 1,2=IR alone, lane 3,4=IR+PTP1B, lane 5,6=IR+RPTPα, lane 7,8=IR +RPTPε, lane 9,10=IR+CD45, lane 11,12=IR+LAR, lane 13,14=IR+PTP1C and lane 15,16=IR+PTPH1.

Figure 4A:
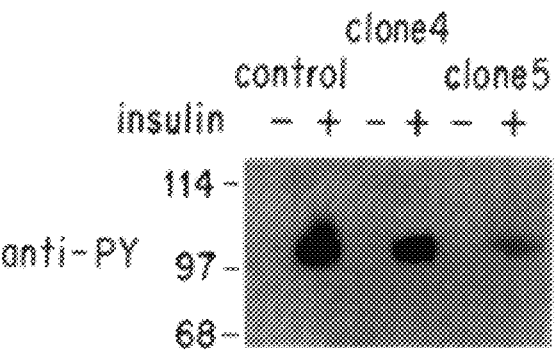

FIG. 4A shows the phosphorylation status of IR in the presence or absence of insulin in two BHK cell clones transfected with the RPTP-α gene: control expressing IR alone, clones 4 and 5 coexpressing IR and RPTPα. The filter was probed with anti-phosphotyrosine (anti-PY) antibodies. The molecular weight in kD is indicated.

Figure 4B:
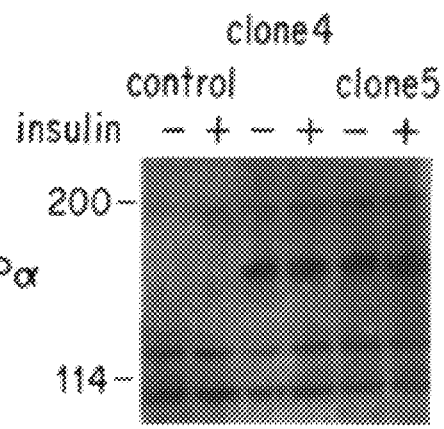

FIG. 4B shows the level of RPTPα expression in the presence or absence of insulin in BHK cell clones: control expressing IR alone, clones 4 and 5 coexpressing IR and RPTPα. The filter was probed with an anti-RPTPα antibody. The molecular weight in kD is indicated.

Figure 4C:
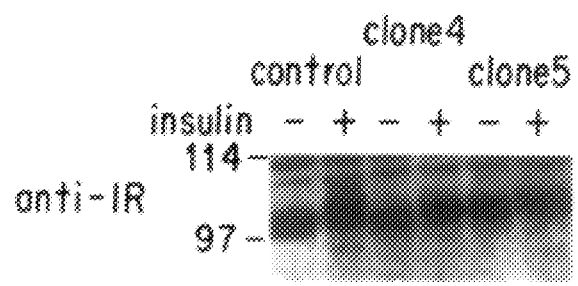

FIG. 4C shows the level of IR expression in the presence or absence of insulin in BHK cell clones: control expressing IR alone, clones 4 and 5 coexpressing IR and RPTPα. The filter was probed with an anti-IR antibody. The molecular weight in kD is indicated.

Figure 5A:
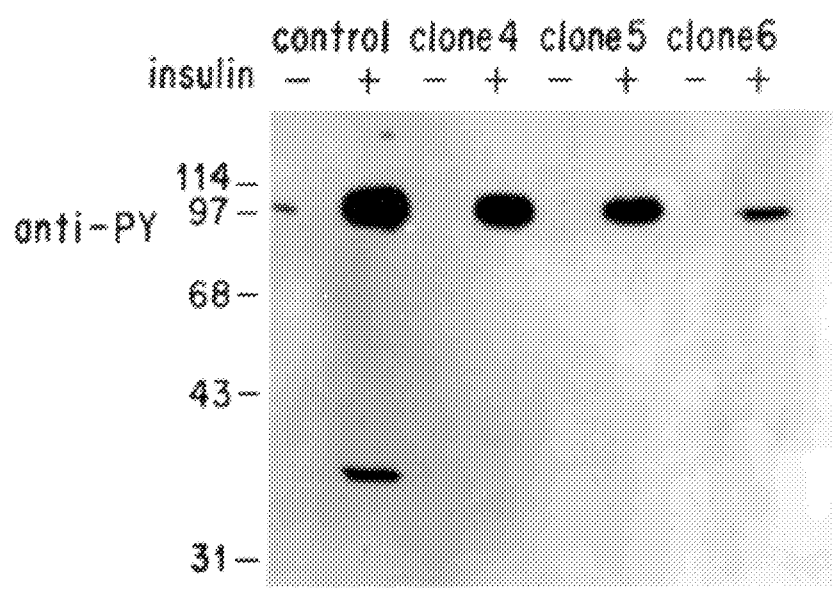

FIG. 5A shows the phosphorylation status of IR in the presence or absence of insulin in BHK cell clones: control expressing IR alone, clones 4, 5 and 6 coexpressing IR and RPTPε. The filter was probed with anti-phosphotyrosine (anti-PY) antibodies. The molecular weight in kD is indicated.

Figure 5B:
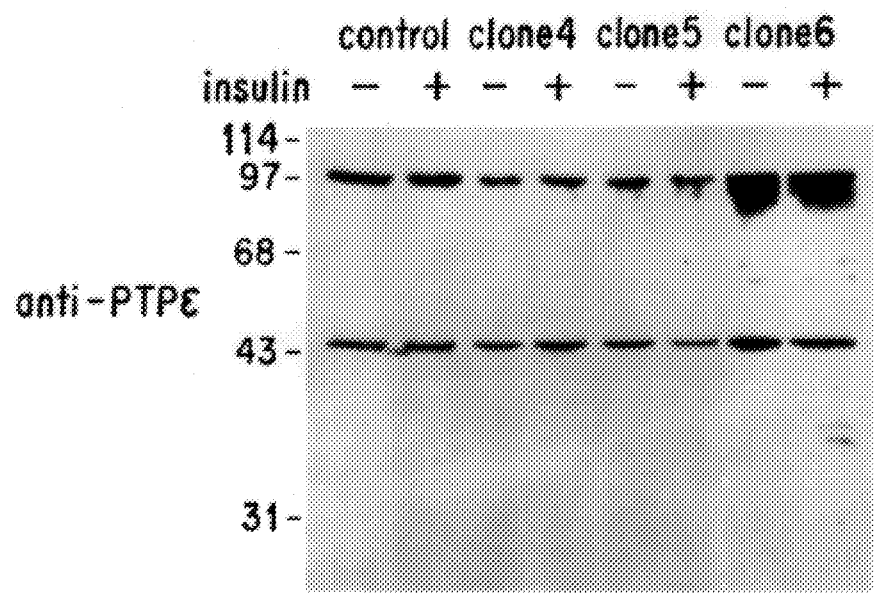

FIG. 5B shows the level of RPTPε expression in the presence or absence of insulin in BHK cell clones: control expressing IR alone, clones 4, 5 and 6 coexpressing IR and RPTPε. The filter was probed with an anti-RPTPε antibody.

Figure 5C:
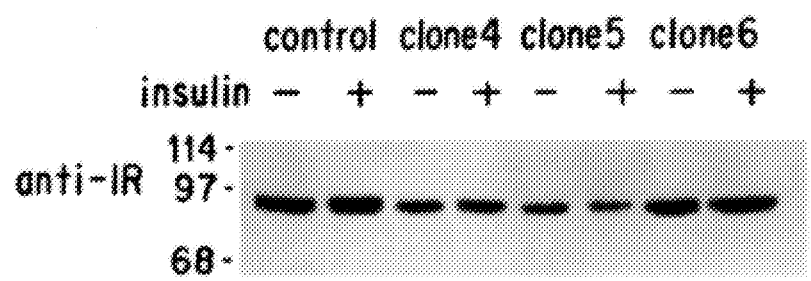

FIG. 5C shows the level of IR expression in the presence or absence of insulin in BHK cell clones: control expressing IR alone, clones 4, 5 and 6 coexpressing IR and RPTPε. The filter was probed with an anti-IR antibody. The molecular weight in kD is indicated.

Figure 6A:
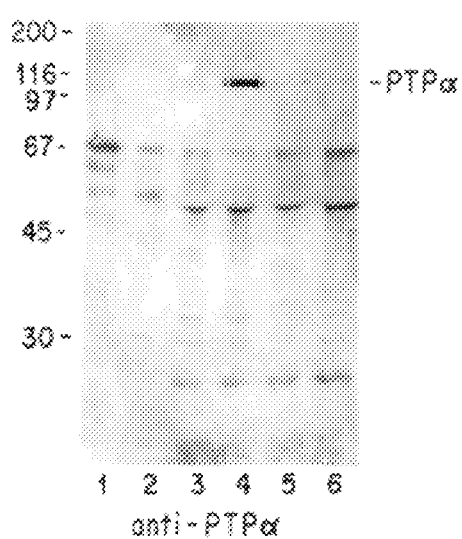

FIG. 6A shows the coimmunoprecipitation of RPTPα with IR by anti-RPTPα antibody. Lanes 1, 2 and 3 are the blank controls for RPTPα, anti-RPTPα antibody and IR respectively. Lane 4 contains RPTPα+IR, lane 5 contains RPTPα+ATP-phosphorylated IR, and lane 6 contains RPTPα+ATPγS-phosphorylated IR. The molecular weight in kD is indicated.

Figure 6B:
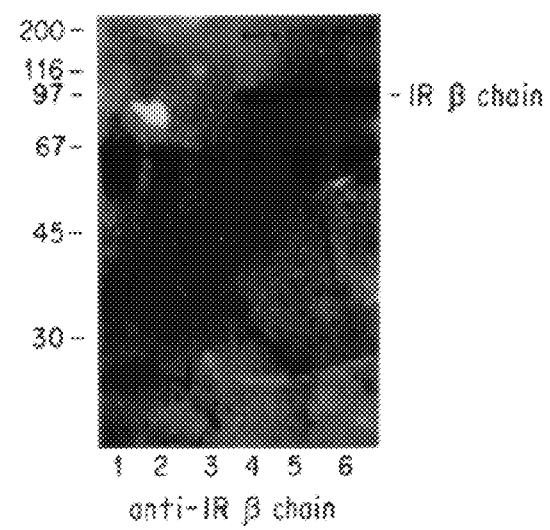

FIG. 6B shows the filter of FIG. 6A after it was washed and reprobed with an anti-IR β chain antibody. The molecular weight in kD is indicated.

Figure 7A:
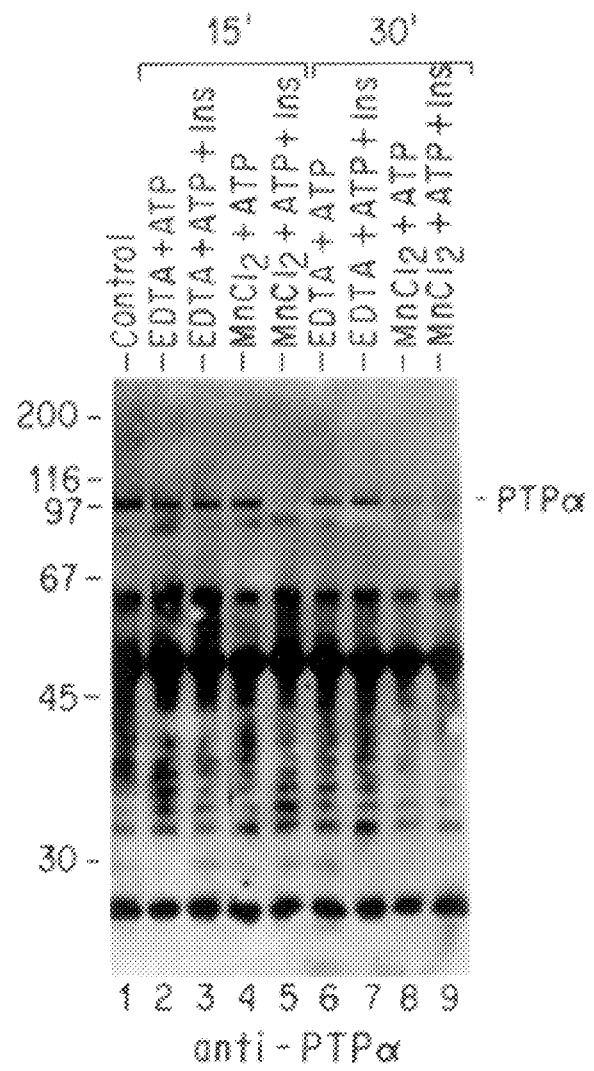

FIG. 7A shows the coimmunoprecipitation of RPTPα and IR by an anti-RPTPα antibody in the presence of EDTA or $MnCl_2$ and/or insulin (Ins) and ATP as indicated. The duration of incubation is indicated: 15 minutes (lanes 2–5) and 30 minutes (lanes 6–9). The filter was probed with an anti-RPTPα antibody. The molecular weight in kD is indicated.

Figure 7B:
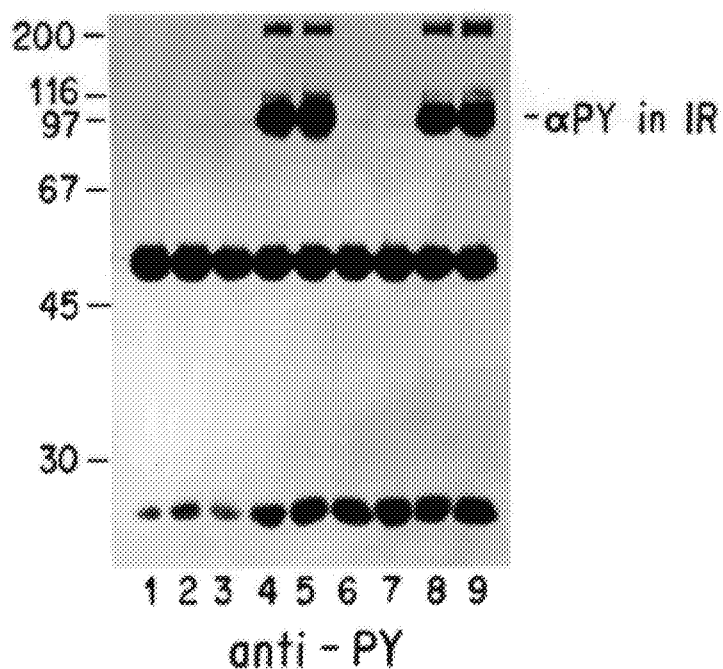

FIG. 7B shows the same filter of FIG. 7A after it was washed and reprobed with an anti-phosphotyrosine (anti-PY) antibody. The molecular weight in kD is indicated.

Figure 7C:
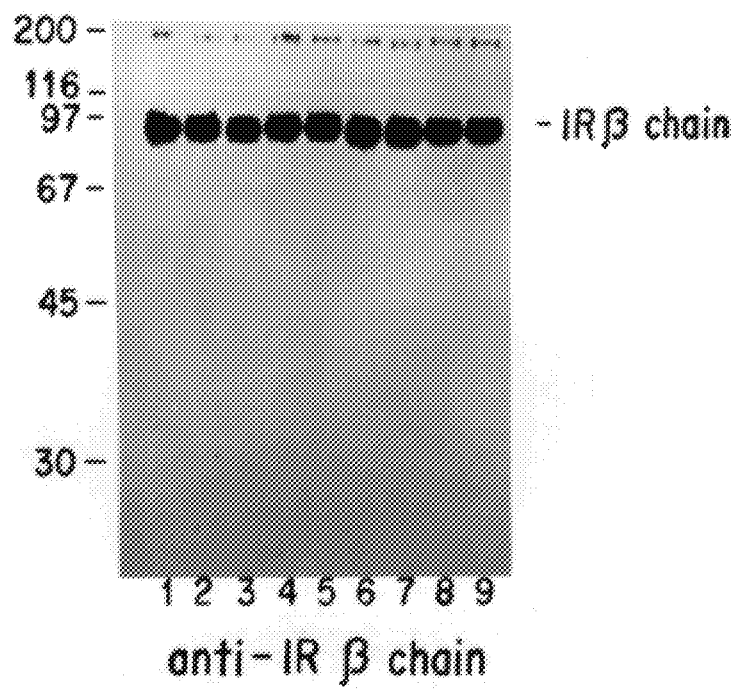

FIG. 7C shows the same blot of FIG. 7B after it was washed and reprobed with an anti-IR β chain antibody. The molecular weight in kD is indicated.

Figure 8:
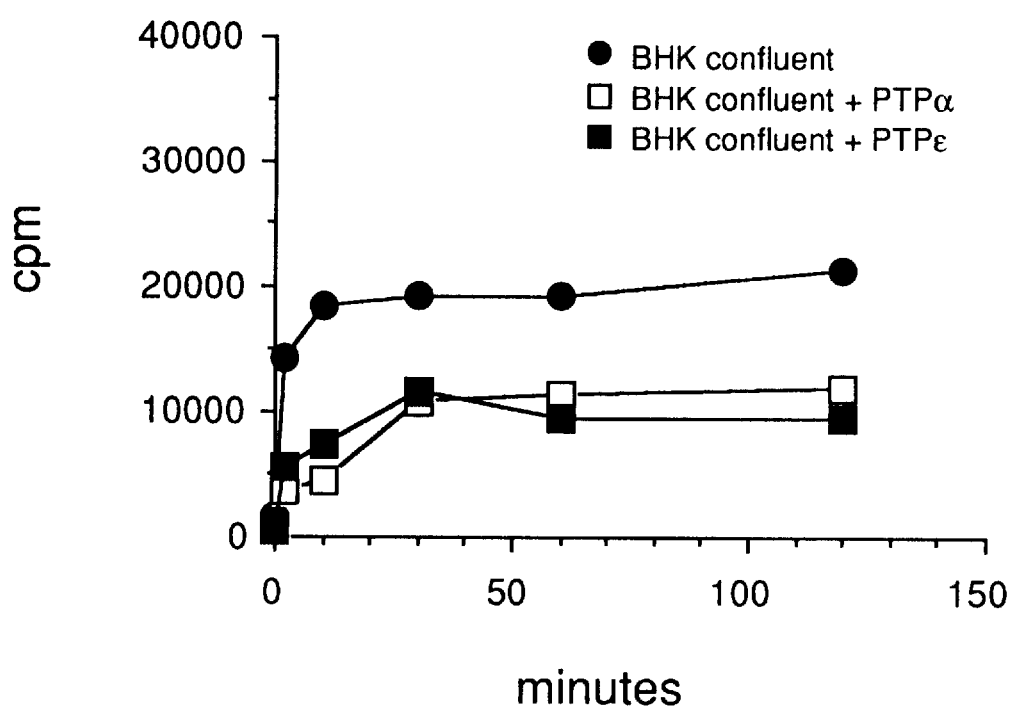

FIG. 8 shows the in vitro kinase activity of IR immunoprecipitated from BHK cells that are coexpressing RPTPα or RPTPε. The amount of radioactivity in counts per minute (cpm) was plotted against incubation time in the presence of insulin in minutes for the indicated cells: ● BHK expressing IR (BHK confluent), □ BHK coexpressing IR and RPTPα (BHK confluent+PTPα) and ■ BHK coexpressing IR and RPTPε (BHK confluent+PTPε).

5. DETAILED DESCRIPTION OF THE INVENTION

The present invention relates to novel modalities for the treatment of diabetes, and other diseases caused by dysfunctional signal transduction by insulin receptor type protein tyrosine kinases (IR-PTKs).

The term signal transduction as used herein is not limited to transmembrane signalling, and includes the multiple pathways that branch off throughout the cell and into the nucleus. Within each individual circuit of the pathway, protein tyrosine kinases and tyrosine phosphatases carry out a series of phosphorylation and dephosphorylation steps which serve to propagate or terminate the signal. The present invention involves the use of compounds, antibodies, nucleic acid molecules or other approaches to modulate the activity of PTPs which are specifically associated with, i.e., specifically dephosphorylate, the insulin receptor-type kinases and/or their downstream tyrosine phosphorylated targets and, therefore, affect signal transduction.

The present invention further relates to methods for screening and identification of compounds that modulate the activity of protein tyrosine phosphatases in the pathway. In a preferred embodiment of the invention, genetically engineered cell lines coexpressing IR and RPTPα or RPTPε may be used in bioassays or to produce reagents for the identification of compounds that may elicit or modulate insulin signal transduction. The action of such novel compounds for treatment of diabetes is not directly based on interactions between insulin and insulin receptor.

In specific embodiments of the present invention detailed in the examples sections infra, the coexpression of IR-PTKs with various PTPs and the resulting patterns of phosphorylation are described. The stable coexpression of IR and RPTPα or RPTPε in BHK cells, and the development of a cell-based assay system for IR signal transduction is also described.

5.1. MODULATION OF PTPs THAT REGULATE IR SIGNAL TRANSDUCTION

Plasma membrane localized RPTPα and RPTPε are RPTPs that specifically regulate the insulin receptor signalling pathway. The specific interaction between these RPTPs and the IR-PTK may involve the formation of a transient or stable multimolecular complex. Cofactor molecules may be recruited, for example, to facilitate the interaction and/or become part of the complex. As used herein, the term ligand is synonymous with extracellular signalling molecules, and includes insulin, IGF-1, IGF-2 and other hormones, growth factors or cytokines that interact with IR-PTKs.

The identification of RPTPα and RPTPε as specific phosphatases that regulate IR-PTK signalling pathways is demonstrated in the working examples infra which demonstrate the specific dephosphorylation of the insulin receptor by RPTPα and RPTPε as well as direct association between the phosphatase and IR and a reduction in IR kinase activity (see Sections 6, 7 and 8 infra). The discovery of this unique activity and association led to the development of the novel modalities of treatment of diseases caused by dysfunctional signal transduction as described below. More specifically, IR-PTK activity can be modified by compounds which modulate the activity of the controlling RPTP, and IR-PTK signal transduction may be triggered, enhanced or prolonged.

A preferred embodiment of the invention is directed to a method of enhancing IR-PTK signal transduction either through the inhibition of RPTP's catalytic activity or through the inhibition of the RPTP's substrate accessibility and/or association. This would allow the insulin receptor to remain activated and generate a signal. It has been shown that IR is phosphorylated at a low level even in the absence of insulin. (Goldstein, 1992, J. Cell Biol., 48:33–42)

For example, the pathogenesis of diabetes generally involves insufficient or a total lack of insulin signal transduction. A diabetic patient's cells do not experience the normal insulin signal and hence, fail to respond to changes in blood glucose level. The paucity or absence of the insulin signal may be caused by a variety of reasons such as a lack of insulin, loss of binding affinity, defective receptor or underexpression of receptor.

IR-PTK activity may be modulated by targeting the phosphatases in the pathway, i.e., RPTPα and RPTPε. In a specific embodiment of the invention, unlike currently available treatment modalities that are based on the insulin receptor, the insulin signal may be restored or stimulated in cells through the inhibition of RPTPα or RPTPε dephosphorylating activity, even in the absence of insulin. To this end, compounds which inhibit RPTPα or RPTPε may be used. Preferably such compound should demonstrate specificity for RPTPα or RPTPε since general inhibitors of all PTPs would be toxic.

In another embodiment of the invention, anti-RPTPα or anti-RPTPε antibodies may be identified that are capable of neutralizing phosphatase activity or capable of preventing the formation of a RPTP-IR-PTK complex. These antibodies may be used to modulate or inhibit RPTPα's or RPTPε's activity on IR-PTK.

In another embodiment of the invention, the nucleic acid sequence encoding the RPTPs may be used to generate recombinant antisense or ribozyme molecules that may be therapeutically useful in modulating the dephosphorylating activity of RPTPs.

For clarity of discussion, the invention is described in the subsections below by way of example for the insulin receptor and diabetes mellitus. However, the principles may be applied to other members of the insulin receptor family of tyrosine kinases such as IGF-1 R and IRR, and other diseases which implicate signal transduction by the respective receptors.

5.1.1. USE OF COMPOUNDS THAT MODULATE THE IR PTP

Any compound which modulates PTP activity involved in regulating the insulin receptor signalling pathway may be used in the therapeutic method of the invention provided the activity of the compound is sufficiently specific for the PTPs. These compounds may be identified by, for example, methods described in section 5.2 or the screening assay system described in section 9.

5.1.2. RPTP ANTIBODIES

Various procedures known in the art may be used for the production of antibodies to epitopes of the recombinantly produced RPTPα, RPTPε, IR, RPTPα-IR and RPTPε-IR complex. Such antibodies include but are not limited to polyclonal, monoclonal, chimeric, single chain, Fab fragments and fragments produced by an Fab expression library. Neutralizing antibodies i.e., those which compete for the substrate binding site of RPTPα or RPTPε, or the IR's site of interaction with RPTPα or RPTPε are especially preferred for therapeutics.

For the production of antibodies, various host animals may be immunized by injection with RPTPα, RPTPε, IR, RPTPα-IR or RPTPε-IR complex including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to RPTPα, RPTPε, IR, RPTPα-IR and RPTPε-IR complex may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce RPTPα, RPTPε, IR, RPTPα-IR or RPTPε-IR complex-specific single chain antibodies.

Antibody fragments which contain specific binding sites of RPTPα, RPTPε, IR, RPTPα-IR or RPTPε-IR complex may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity to RPTPα, RPTPε, IR, RPTPα-IR or RPTPε-IR complex.

5.1.3. GENE THERAPY

Target cell populations may be modified by introducing altered forms of RPTPα or RPTPε in order to modulate the activity of endogenously expressed RPTPs. By reducing or inhibiting the biological activity of wild type RPTPα or RPTPε, the target cells' IR kinase activity may be increased to facilitate or trigger insulin signal transduction.

Deletion or missense mutants of RPTPα or RPTPε that retain the ability to interact with IR but cannot function in signal transduction may be used to displace the endogenous wild type phosphatase. The mutant RPTP may have a dominant effect if it is overexpressed or if its interaction with IR is more potent than the wild type. For example, the phosphatase domain of RPTPα or RPTPε may be deleted resulting in a truncated molecule that is still able to interact with IR.

Expression vectors derived from viruses such as retroviruses, vaccinia virus, adeno-associated virus, herpes viruses, or bovine papilloma virus, may be used for delivery of recombinant RPTPα or RPTPε into the targeted cell population. Methods which are well known to those skilled in the art can be used to construct recombinant viral vectors containing PTP coding sequences. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant RPTPs and/or IR-PTK nucleic acid molecules can be used as naked DNA or in a reconstituted system e.g., liposomes or other lipid systems for delivery to target cells (See e.g., Felgner et al., 1989, Nature 337:387–8).

5.1.4. ANTISENSE AND RIBOZYME APPROACHES

Included in the scope of the invention are oligoribonucleotides, that include antisense RNA and DNA molecules and ribozymes that function to inhibit translation of RPTPα or RPTPε mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the PTP and/or PTK nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of RPTPα or RPTPε RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

5.1.5. PHARMACEUTICAL FORMULATIONS AND MODES OF ADMINISTRATION

The particular compound, antibody, antisense or ribozyme molecule that modulate the PTP targets of the invention can be administered to a patient either by itself, or in pharmaceutical compositions where it is mixed with suitable carriers or excipient(s).

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the PTP activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

5.2. ASSAY SYSTEMS FOR DRUG SCREENING

In another embodiment of the invention, the nucleic acid sequence encoding the RPTPs, i.e., RPTPα or RPTPε, or IR-PTKs may be used to generate recombinant nucleic acid molecules that direct the expression of RPTPs and/or IR-PTK or a functional equivalent thereof, in appropriate host cells. Such engineered cells may be used in producing RPTPs and/or IR-PTK proteins, or RPTP-IR-PTK complexes, or in generating antibodies, or in gene therapy. A RPTP-IR-PTK complex is a complex comprising a IR-PTK and either RPTPα or RPTPε. In yet another embodiment of the invention, such engineered cells may also be used for identifying other specific RPTP proteins or genes that are involved in the insulin signalling pathway.

The RPTP proteins or RPTP-IR-PTK complex, or cell lines that express the RPTPs or RPTP-IR-PTK complex, may be used to screen for compounds, antibodies, or other molecules that act as inhibitors of RPTPα and/or RPTPε activity on IR-PTKs, or interfere with the formation of a RPTP-IR-PTK complex. Recombinantly expressed RPTPs or RPTP-IR-PTK complex, or cell lines expressing RPTPs or RPTP-IR-PTK complex may be used to screen peptide libraries, natural products extracts or chemical libraries.

Such compounds, antibodies or other molecules so identified may be used in the therapeutic methods of the invention.

Moreover, the assays can be utilized to determine therapeutically effective doses of the test compound. For example, when screening for inhibitors of the PTP, the IC50 (i.e., the concentration of the test compound which achieves a half-maximal inhibition of the PTP activity) for each compound can be determined in cell culture or whole animals. Doses in animals can initially be formulated to achieve the IC50 concentration in the circulation. Toxicity and therapeutic efficacy of inhibitors so identified can be determined by routine procedures, e.g. for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The specific therapeutic benefits of such compounds can also be studied and measured in established models of the disease in experimental animals, for example, non-obese diabetic mice (Lund et al., 1990, Nature 345:727–9), BB Wistar rats and streptozotocin-induced diabetic rats (Solomon et al., 1989 Am. J. Med. Sci. 297:372–6). Other useful animal models for Type I and Type II diabetes are described in Makino et al., (1980, Exp. Anim. (Tokyo) 29:1–14) and Michaelis et al. (1986, Am. J. Pathol. 123:398–400) respectively. The data obtained from these cell culture assays and animal studies can be used in formulating a range of dosages for use in humans. The dosage of such compounds should lie within a range of circulating concentrations that include the ED50 with little or no toxicity. The dosage may vary within this range depending upon the dosage form employed and the route of administration utilized. (See e.g., The Merck Manual, 1987, 15th ed., Vol. 1, Ch. 277, p. 2461).

The assays are exemplary and not intended to limit the scope of the method of the invention. Those of skill in the art will appreciate that modifications can be made to the assay system to develop equivalent assays that obtain the same result.

5.2.1. COEXPRESSION OF RPTPS AND IR-PTK AND GENERATION OF ENGINEERED CELL LINES

In accordance with one aspect of the invention, RPTPα, RPTPε and IR nucleotide sequences or functional equivalents thereof may be used to generate recombinant DNA molecules that direct the coexpression of RPTPα or RPTPε and IR proteins or a functionally equivalent thereof, in appropriate host cells. The nucleotide sequences of RPTPα, RPTPε and IR are reported in Sap et al., 1990, Proc. Natl. Acad. Sci. USA, 87:6112–6 and Kaplan et al., 1990, Proc. Natl. Acad. Sci. USA, 87:7000–4; Krueger et al., 1990, EMBO J, 9:3241–52; and Ullrich et al., 1985, Nature 313:756–61 respectively and are incorporated by reference herein in their entirety. As used herein, a functionally equivalent RPTPα, RPTPε or IR refers to an enzyme with essentially the same catalytic function, but not necessarily the same catalytic activity as its native counterpart. A functionally equivalent receptor refers to a receptor which binds to its cognate ligand, but not necessarily with the same binding affinity of its counterpart native receptor.

Due to the inherent degeneracy of the genetic code, other DNA sequences which encode substantially the same or a functionally equivalent amino acid sequence, may be used in the practice of the invention for the coexpression of the RPTPα or RPTPε and IR proteins. Altered DNA sequences which may be used in accordance with the invention include deletions, additions or substitutions. For example, mutations may be introduced using techniques which are well known in the art, e.g. site-directed mutagenesis, to insert new restriction sites, to alter glycosylation patterns, phosphorylation, etc. Amino acid substitutions may be made on the basis of similarity in polarity, charge, solubility, hydrophobicity, hydrophilicity, and/or the amphipatic nature of the residues involved. Any nucleotide sequence that hybridizes to the RPTPα, RPTPε or IR coding sequence and/or its complement can be utilized, provided that the resulting gene product has activity.

The RPTPα, RPTPε or IR or a modified RPTPα, RPTPε or IR sequence may be ligated to a heterologous sequence to encode a fusion protein. For example, for screening of peptide libraries it may be useful to encode a chimeric RPTPα, RPTPε or IR protein expressing a heterologous epitope that is recognized by an antibody. A fusion protein may also be engineered to contain the ligand-binding, regulatory or catalytic domain of another PTP or PTK.

The coding sequence of RPTPα, RPTPε or IR could be synthesized in whole or in part, using chemical methods well known in the art. See, for example, Caruthers, et al., 1980, Nuc. Acids Res. Symp. Ser. 7:215–233; Crea and Horn, 180, Nucleic Acids Res. 9(10):2331; Matteucci and Caruthers, 1980, Tetrahedron Letters 21:719; and Chow and Kempe, 1981, Nucleic Acids Res. 9(12):2807–2817.

In order to coexpress a biologically active RPTPα, RPTPε or IR, the nucleotide sequence coding for RPTPα, RPTPε or IR, or their functional equivalent as described supra, is inserted into one or more appropriate expression vector(s), i.e., a vector which contains the necessary elements for the transcription and translation of the inserted coding sequence (s). The RPTPα and/or RPTPε gene(s) may be placed in tandem with the IR sequence under the control of the same or different promoter used to control the expression of the other coding sequence. The two phosphatases, RPTPα and RPTPε may also be both coexpressed together with IR.

Methods which are well known to those skilled in the art can be used to construct expression vectors containing the RPTPα, RPTPε and/or IR coding sequence(s) and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to coexpress the RPTPα, RPTPε, or IR coding sequences. These include but are not limited to microorganisms such as bacteria transformed with recombinant bacteriophage DNA, plasmid DNA or cosmid DNA expression vectors containing the RPTPα, RPTPε, or IR coding sequence(s) (see, Current Protocols in Molecular Biology, Vol. 2, 1988, Ed. Ausubel et al., Greene Publish. Assoc. & Wiley Interscience, Section 16.1); yeast transformed with recombinant yeast expression vectors containing the RPTPα, RPTPε, or IR coding sequence(s) (Bitner, Heterologous Gene Expression in Yeast, Meths Enzymol, Eds. Berger & Mimmel, Acad. Press, N.Y. 152:673–84, 1987); insect cell systems infected with recombinant virus expression vectors (e.g., baculovirus, see Smith et al., 1983, J. Viol. 46:584; Smith, U.S. Pat. No. 4,215,051) containing the RPTPα, RPTPε and/or IR coding sequence(s); plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the RPTPα, RPTPε and/or IR coding sequence(s) (see Weissbach & Weissbach, 1988, Methods for Plant Molecular Biology, Academic Press, N.Y.); or animal cell systems.

In mammalian host cells, a number of viral based expression systems may be utilized. (E.g., See Logan & Shenk, 1984, Proc. Natl. Acad. Sci. (USA) 81:3655–3659, Mackett et al., 1982, Proc. Natl. Acad. Sci. (USA) 79:7415–7419; Mackett et al., 1984, J. Virol. 49:857–864).

A host cell of a particular cell type may also be chosen for the cell type specific cofactors which may be required for the signal pathway. A host cell strain may also be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38 and PC12.

For long-term, high-yield production of recombinant proteins in animal cells, stable expression is preferred. For example, cell lines which stably coexpress RPTPα and/or RPTPε and IR may be engineered. Rather than using expression vectors which contain viral origins of replication, host cells can be transformed with RPTPα, RPTPε, or IR DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which coexpress both the RPTP and IR-PTK, and which respond to ligand mediated signal transduction. Such engineered cell lines are particularly useful in screening PTP inhibitors stimulators and analogs.

A number of selection systems may be used (Kaufman, 1990, Meth. Enzymol. 185:537–66) including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻or aprt⁻ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre- Garapin, et al., 1981, J. Mol. Biol. 150:1); and hygro, which confers resistance to hygromycin (Santerre, et al., 1984, Gene 30:147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

As the IR-PTK and RPTP may be coexpressed from different expression plasmids in the same cell, a different amplifiable selection system (for example, dhfr and adenosine deaminase) may be used for each individual plasmid. By applying different concentrations of the selecting drugs, the expression level of individual protein may be controlled separately as required (Wood et al., J. Immunol. 145:3011–16, 1990).

The host cells which contain the coding sequences and which express the biologically active gene products may be identified by at least three general approaches; (a) DNA-DNA or DNA-RNA hybridization; (b) the presence or absence of "marker" gene functions; and (c) detection of the gene products as measured by immunoassay or by their biological activity.

In the first approach, the presence of the RPTPα, RPTPε or IR coding sequence(s) inserted in the expression vector(s) can be detected by DNA-DNA or DNA-RNA hybridization using probes comprising nucleotide sequences that are homologous to the RPTPα, RPTPε or IR coding sequence (s), respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the RPTPα, RPTPε or IR coding sequence(s) is inserted within a marker gene sequence of the vector, recombinants containing the RPTPα, RPTPε or IR coding sequence(s) can be identified by the absence of the marker gene function. Alternatively, a marker gene can be placed in tandem with the RPTPα, RPTPε or IR sequence under the control of the same or different promoter used to control the expression of the RPTPα, RPTPε or IR coding sequence(s). Expression of the marker in response to induction or selection indicates expression of the RPTPα, RPTPε or IR coding sequence(s).

In the third approach, the expression of the RPTPα, RPTPε or IR protein product can be assessed immunologically, for example by Western blots, immunoassays such as immunoprecipitation, enzyme-linked immunoassays and the like. The ultimate test of the success of the expression system, however, involves the detection of the biologically active RPTPα, RPTPε or IR proteins. A number of assays can be used to detect activity including but not limited to ligand binding assays, phosphorylation assays, dephosphorylation assays; and biological assays using engineered cell lines as the test substrate.

The RPTPα, RPTPε or IR gene products as well as host cells or cell lines transfected or transformed with recombinant RPTPα, RPTPε and IR expression vector(s) can be used for a variety of purposes. These include but are not limited to the screening and selection of proteins that are structurally analogous to RPTPα or RPTPε that bind to but not dephosphorylate IR; or drugs that act via the interaction or complex formed between RPTPα and IR, or RPTPε and IR; or generating antibodies (i.e., monoclonal or polyclonal) that bind to the RPTPα-IR or RPTPε-IR complex, including those that competitively inhibit the formation of such complexes. These gene products or host cells or cell lines may also be used for identifying other signalling molecules or their genes that are engaged in the insulin signalling pathway.

5.2.2. SCREENING ASSAYS

The RPTPs, the RTP-IR-PTK complex, or cell lines that express the RPTPs and/or IR complex, may be used to screen for molecules that modulate RTP activity. Such molecules may include small organic or inorganic compounds, antibodies, peptides, or other molecules that modulate RPTPα's or RPTPε's dephosphorylation activity toward IR, or that promote or prevent the formation of RPTPα-IR or RPTPε-IR complex. Synthetic compounds, natural products, and other sources of potentially biologically active materials can be screened in a number of ways.

The ability of a test molecule to modulate the activity of RPTPα or RPTPε toward IR, hence signal transduction, may be measured using standard biochemical techniques, such as those described in Section 6.1. Other responses such as activation or suppression of catalytic activity, phosphorylation or dephosphorylation of other proteins, activation or modulation of second messenger production, changes in cellular ion levels, association, dissociation or translocation of signalling molecules, gene induction or transcription or translation of specific genes may also be monitored. These assays may be performed using conventional techniques developed for these purposes in the course of screening.

Ligand binding to its cellular receptor may, via signal transduction pathways, affect a variety of cellular processes. Cellular processes under the control of insulin signalling pathway may include, but are not limited to, normal cellular functions such as carbohydrate metabolism, proliferation, differentiation, maintenance of cell shape, and adhesion, in addition to abnormal or potentially deleterious processes such as apoptosis, loss of contact inhibition, blocking of differentiation or cell death. The qualitative or quantitative observation and measurement of any of the described cellular processes by techniques known in the art may be advantageously used as a means of scoring for signal transduction in the course of screening.

Applicants have observed that BHK cell lines overexpressing IR (IR/BHK) exhibit a dramatically altered and abnormal phenotype in the presence of high concentrations of insulin. The novel selection system for IR receptor activation based on this observation is described in Section 7.

Various embodiments are described below for screening, identification and evaluation of compounds that interact with RPTPα, RPTPε and IR, which compounds may affect various cellular processes under the control of the insulin receptor signalling pathway.

The present invention includes a method for identifying a compound which is capable of, by modulating tyrosine phosphatase activity of RPTPα and/or RPTPε, modulating insulin receptor-type protein kinase IR-PTK signal transduction, comprising:

(a) contacting the compound with RPTPα and/or, RPTPε and IR or, functional derivatives thereof, in pure form, in a membrane preparation, or in a whole live or fixed cell;

(b) incubating the mixture of step (a) for an interval sufficient for the compound to stimulate or inhibit the tyrosine phosphatase enzymatic activity or the signal transduction;

(c) measuring the tyrosine phosphatase enzymatic activity or the signal transduction;

(d) comparing the phosphotyrosine phosphatase enzymatic activity or the signal transduction activity to that of RPTPα and/or RPTPε and IR, incubated without the compound, thereby determining whether the compound stimulates or inhibits signal transduction.

RPTPα and/or RPTPε and IR, or functional derivatives thereof, for example, having amino acid deletions and/or insertions and/or substitutions while maintaining signal transduction, can also be used for the testing of compounds. A functional derivative may be prepared from a naturally occurring or recombinantly expressed RPTPα, RPTPε and IR by proteolytic cleavage followed by conventional purification procedures known to those skilled in the art. Alternatively, the functional derivative may be produced by recombinant DNA technology by expressing parts of RPTPα, RPTPε or IR which include the functional domain in suitable cells. Cells expressing RPTPα and/or RPTPε and IR may be used as a source of RPTPα, RPTPε and/or IR, crude or purified, or in a membrane preparation, for testing in these assays. Alternatively, whole live or fixed cells may be used directly in those assays. The cells may be genetically engineered to coexpress RPTPα, RPTPε and IR. The cells may also be used as host cells for the expression of other recombinant molecules with the purpose of bringing these molecules into contact with RPTPα, RPTPε and/or IR within the cell.

IR-PTK signal transduction activity may be measured by standard biochemical techniques or by monitoring the cellular processes controlled by the signal. To assess modulation of phosphatase activity, the test molecule is added to a reaction mixture containing the phosphorylated substrate and the phosphatase. To assess modulation of kinase activity of the IR-PTK, the test molecule is added to a reaction mixture containing the IR-PTK and its substrate (in the case of autophosphorylation, the IR-PTK is also the substrate). Where the test molecule is intended to mimic ligand stimulation, the assay is conducted in the absence of insulin. Where the test molecule is intended to reduce or inhibit insulin activity, the test is conducted in the presence of insulin. The kinase reaction is then initiated with the addition of ATP. An immunoassay is performed on the kinase or phosphatase reaction to detect the presence or absence of the phosphorylated tyrosine residues on the substrate, and results are compared to those obtained for controls i.e., reaction mixtures not exposed to the test molecule. The immunoassay used to detect the phosphorylated substrate in the cell lysate or the in vitro reaction mixture may be carried out with an anti-phosphotyrosine antibody.

Signal transduction is mimicked if the cellular processes under the control of the signalling pathway are affected in a way similar to that caused by ligand binding. Such compounds may be naturally occurring or synthetically produced molecules that could replace the administration of insulin in the treatment of diabetes.

The invention also includes a method whereby a molecule capable of binding to RPTPα and/or RPTPε and IR in a chemical or biological preparation may be identified comprising:

(a) immobilizing RPTPα and/or RPTPε and IR, or fragments thereof, to a solid phase matrix;

(b) contacting the chemical or biological preparation with the solid phase matrix produced in step (a), for an interval sufficient to allow the compound to bind;

(c) washing away any unbound material from the solid phase matrix;

(d) detecting the presence of the compound bound to the solid phase, thereby identifying the compound.

The above method may further include the step of:

(e) eluting the bound compound from the solid phase matrix, thereby isolating the compound.

The term "compound capable of binding to RPTPα and/or RPTPε and IR" refers to a naturally occurring or synthetically produced molecule which interacts with RPTPα and/or RPTPε and IR. Such a compound may directly or indirectly modulate IR-PTK signal transduction and may include molecules that are natively associated with RPTPα, RPTPε and/or IR inside a cell. Examples of such compounds are (i) a natural substrate of RPTPα and/or RPTPε; (ii) a naturally occurring molecule which is part of the signalling complex; iii) a natural substrate of IR-PTK, iv) a naturally occurring signalling molecule produced by other cell types.

The present invention also includes methods for identifying the specific site(s) of RPTPα, or RPTPε interaction with IR. Using the methods described herein, and biochemical and molecular biological methods well-known in the art, it is possible to identify the corresponding portions of RPTPα, RPTPε and IR involved in this interaction. For example, site-directed mutagenesis of DNA encoding either RPTPα, RPTPε or IR may be used to destroy or inhibit the interaction between the two molecules. Biophysical methods such as X-ray crystallography and nuclear magnetic resonance may also be used to map and study these sites of interaction. Once these sites have been identified, the present invention provides means for promoting or inhibiting this interaction, depending upon the desired biological outcome. Based on the foregoing, given the physical information on the sites of interaction is known, compounds that modulate catalytic activity and signal transduction may be elaborated by standard methods well known in the field of rational drug design.

The present invention further provides an assay for identifying a compound, which can block the interaction of RPTPα or RPTPε and IR. For example, a cell transfected to coexpress RPTPα or RPTPε and IR, in which the two proteins interact to form a RPTPα-IR or RPTPε-IR complex, can be incubated with an agent suspected of being able to inhibit this interaction, and the effect on the interaction measured. Any of a number of means for measuring the interaction and its disruption such as coimmunoprecipitation are available. The present invention also provides an assay method to identify and test a compound which stabilizes and promotes the interaction, using the same approach described above for a potential inhibitor.

Random peptide libraries consisting of all possible combinations of amino acids may be used to identify peptides that are able to bind to the substrate binding site of RPTPα or RPTPε, or other functional domains of RPTPα or RPTPε. Similarly, such libraries may also be used to identify peptides that are able to bind to the IR's site of interaction with RPTPα or RPTPε. Identification of molecules that are able to bind to RPTPα, RPTPε and IR may be accomplished by screening a peptide library with recombinant RPTPα, RPTPε or IR proteins or recombinant soluble forms of RPTPα or RPTPε or IR protein. Alternatively, the phosphatase and extracellular ligand binding domains of RPTPα or RPTPε may be separately expressed and used to screen peptide libraries.

One way to identify and isolate the peptide that interacts and forms a complex with RPTPα or RPTPε and IR, may involve labelling or "tagging" RPTPα or RPTPε and IR proteins. The RPTPα or RPTPε and IR proteins may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label, to RPTPα or RPTPε and IR, may be performed using techniques that are routine in the art. Alternatively, RPTPα, RPTPε or IR expression vectors may be engineered to express a chimeric RPTPα, RPTPε or IR protein containing an epitope for which a commercially available antibody exists. The epitope-specific antibody may be tagged using methods well known in the art including labeling with enzymes, fluorescent dyes or colored or magnetic beads.

The present invention also includes a method for identifying and isolating a nucleic acid molecule encoding a gene product which is capable of, by modulating tyrosine phosphatase activity RPTPα and/or RPTPε, modulating IR-PTK signal transduction, comprising:

(a) introducing the nucleic acid molecule into host cells coexpressing RPTPα and/or RPTPε and IR or fragments thereof;

(b) culturing the cells so that the gene product encoded by the nucleic acid molecule is expressed in the host cells and interacts with RPTPα and/or RPTPε and IR or fragments thereof;

(c) measuring the tyrosine phosphatase enzymatic activity of RPTPα and/or RPTPε or IR-PTK signal transduction activity;

(d) comparing the tyrosine phosphatase enzymatic activity or signal transduction to that of RPTPα and/or RPTPε and IR, or fragments thereof in cells without the nucleic acid molecule, thereby determining whether the gene product encoded by the nucleic acid molecule modulates IR-PTK signal transduction.

The above method may further include the step of:

(e) selecting and culturing the cells identified in step (d), recovering the nucleic acid molecule, thereby isolating the nucleic acid molecule.

By the term "nucleic acid molecule" is meant a naturally occurring or recombinantly generated nucleic acid molecule containing a nucleotide sequence operatively associated with an element that controls expression of the nucleotide sequence. An expression library may be created by introducing into host cells a pool of different nucleic acid molecules encoding different gene products. The host cells may be genetically engineered to coexpress RPTPα, RPTPε and IR. Such a gene library may be screened by standard biochemical techniques or by monitoring the cellular processes controlled by the signal. This approach is especially useful in identifying other native signalling molecules that are also involved in the signalling pathway.

Having now generally described the invention, the same will be more readily understood through reference to the following examples which are provided by way of illustration, and are not intended to be limiting of the present invention.

6. EXAMPLE: TRANSIENT COEXPRESSION OF THE INSULIN RECEPTOR AND PTP

The subsections below describe the transient coexpression of insulin receptor (IR) and various phosphotyrosine phosphatases (PTPs) in 293 cells to investigate the effect of PTP expression on the phosphorylation state of IR. In particular, RPTPα, RPTPε, TC-PTP, CD45, LAR, PTP1B, PTP1C and PTPH1 were individually coexpressed with the IR to identify PTPs which are specifically associated with IR activity. The results show that RPTPα and RPTPε specifically dephosphorylate the IR and interfere with signal transduction.

6.1. MATERIAL AND METHODS

All cDNAs were cloned into a cytomegalovirus early promoter-based expression plasmid pCMV (Eaton et al., 1986, Biochemistry 25:8343–47). CsCl gradient purified DNA was used for transfections. Human embryonic kidney fibroblast 293 cells (ATCC CRL 1573) were grown, transfected, and analyzed as described in Lammers et al. (J. Biol Chem. 265:16886–90, 1990). Briefly, cells were grown in F12/DMEM 50:50, with 10% fetal calf serum, 2 mM L-glutamine, and antibiotics.

Two μg of plasmid DNA for RTK or PTP were transfected into $3 \times 10^5$ cells/10-cm$^2$ well according to the protocol of Chen and Okayama (Mol. Cell Biol., 7:2745–52, 1987). For the experiment including insulin receptor substrate-1 (IRS-1, Sun et al., 1991, Nature, 352:73–7), 1.5 μg of each expression plasmid was used. When different amounts or mixtures of expression plasmids were used for transfections, the DNA concentration for the generation of the CaCl$_2$ precipitate was adjusted to 20 μg/ml (22.5 for the experiment including IRS-1) with herring sperm DNA. Eighteen hours after the addition of DNA precipitate, cells were washed once and supplied with fresh medium containing 0.5% serum. Twenty-four hours later, cells were stimulated with ligand (insulin and IGF-1 for IR and IGF-1 R respectively, 1 μg/ml) for 10 minutes and then lysed in 200 μl lysis buffer (50 mM HEPES, pH 7.2, 150 mM NaCl, 1.5 mM MgCl$_2$, 1 mM EGTA, 10% glycerol, 1% Triton X-100, 2 mM phenylmethylsulfonyl fluoride, 10 μg/ml aprotinin, 100 mM NaF, 10 mM sodium pyrophosphate and 1 mM Na-orthovanadate). The lysate was centrifuged for 2 minutes at 12500 g and 30 μl of the supernatant was taken. Sample buffer (1x: 2% SDS, 100 mM dithiothreitol, 60 mM Tris pH6.8, 0.01% bromophenol blue) was added and the sample was boiled for 10 minutes, and then analyzed by SDS-PAGE and immunoblotting. Blots were probed using the mouse monoclonal antiphosphotyrosine antibody 5E2 (Fendly et al., Cancer Res., 50:1550–8, 1990). Detection of phosphotyrosine on immunoblots was done using the ECL system (Amersham) in conjunction with goat anti-mouse and antibodies (Biorad).

6.2. RESULTS

6.2.1. IR-PTK DEPHOSPHORYLATION BY RPTPα AND RPTPε

RPTPα, RPTPε, TC-PTP and an inactive mutant, TC-C (in which cysteine 216 had been mutated to serine) were coexpressed with IR or IGR-1R in 293 cells. After stimulation with the appropriate ligand for 10 minutes, the cells were lysed and aliquots of the cell lysate were analyzed by SDS-PAGE. The size separated proteins were transferred to nitrocellulose and probed with an anti-phosphotyrosine antibody.

Figure 1:
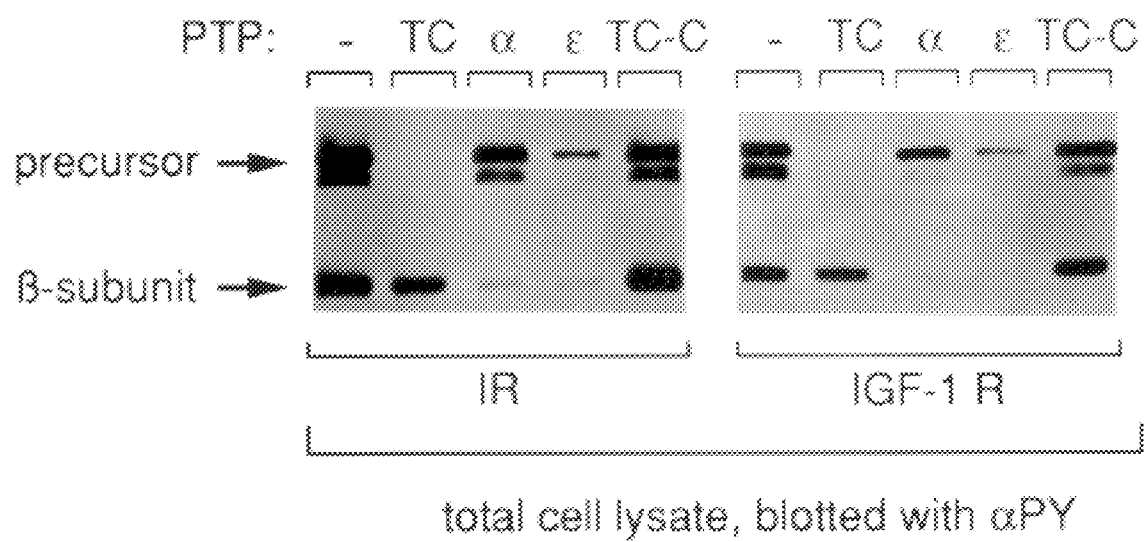

FIG. 1 shows the analysis of phosphotyrosine content of IR and IGF-1 R expressed alone or together with one of the PTPs. Members of the insulin receptor-type family are synthesized as inactive precursor polypeptides which are proteolytically cleaved into ligand-binding a and tyrosine kinase domain containing β subunits during their transport to the cell surface. In comparison to cells expressing the receptor alone, RPTPα and RPTPε completely dephosphorylated the β subunits of the two mature, active receptors while the precursor forms remain phosphorylated. The wild type TC-PTP dephosphorylated only the precursor forms but not the mature receptors. TC-PTP is a cytoplasmic PTP normally found associated with the endoplasmic reticulum inside the cell (Cool et al., Proc. Natl. Acad. Sci. USA, 86:5257, 1989).As an additional control, receptor cotransfected with the inactive TC-C showed a similar degree of phosphorylation as that of receptor alone.

6.2.2. SPECIFIC DEPHOSPHORYLATION OF IR BY RPTPα AND RPTPε

Figure 2:
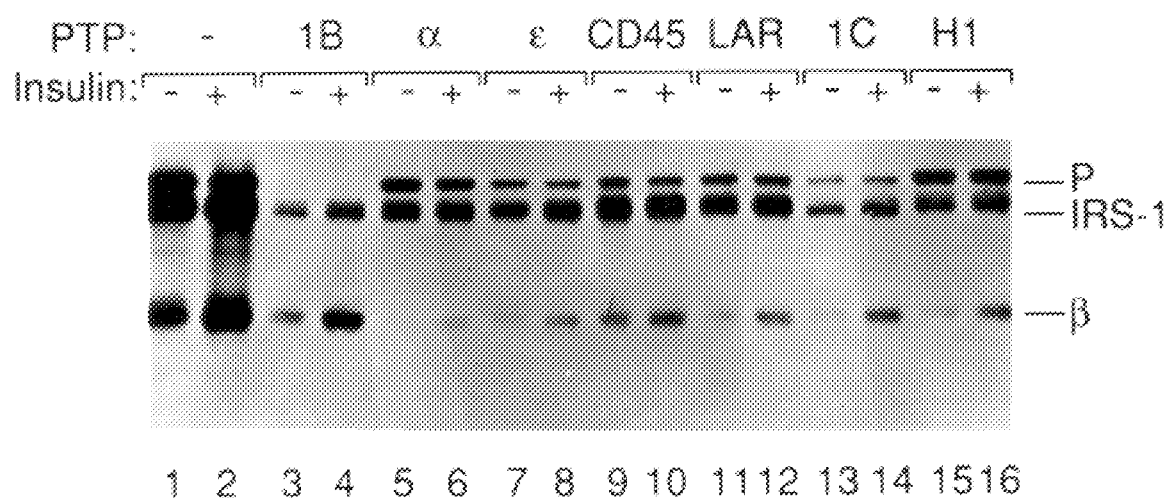

Further evidence of the specificity of RPTPα and RPTPε for the IR, was obtained by individually coexpressing seven transmembrane and cytoplasmic phosphatases, (RPTPα, RPTPε, CD45, LAR, PTP1B, PTP1C and PTPH1) with IR in 293 cells. The cells were treated with insulin for 10 minutes before lysis and proteins present in the cell lysates were separated by SDS-PAGE and transferred to nitrocellulose. Tyrosine phosphorylated proteins were detected by immunoblotting with anti-phosphotyrosine antibody. As shown in FIG. 2, RPTPα and RPTPε were the most effective RPTPs in dephosphorylating the β subunit of IR which is the subunit involved in signal transduction although all the phosphatases tested showed some dephosphorylating activity of the three IR substrates, IRS-1, the IR precursor and IR β subunit. PTP1B, which is localized on the cytoplasmic face of the endoplasmic reticulum, was the only PTP effective in dephosphorylating the precursor form of IR. The results show that PTPs are selective in their choice of substrates and this selectivity appears to be partly defined by cellular compartmentalization.

7. EXAMPLE: DEMONSTRATION OF AN IN VIVO SELECTION SYSTEM FOR INSULIN RECEPTOR ACTIVATION

In the example described below, host cells were engineered to express both the IR and a series of PTPs. The cells expressing IR alone or IR plus an ineffective PTP display an altered phenotype when exposed to insulin. The results show that co-expression of RPTPα or RPTPε inhibits phosphorylation of the IR and restores normal cell phenotype. The results demonstrate that RPTP-α and RPTP-ε modulate with IR signal transduction.

7.1. MATERIALS AND METHODS

IR/BHK cells were maintained in DMEM/high glucose, 10% fetal calf serum, 10 mM glutamine, 1 μM methotrexawere plus antibiotics. The cDNAs for RPTPα or RPTPε were cloned into a cytomegalovirus early promoter-based expression plasmid pCMV (Eaton et al., 1986, Biochemistry, 25:8343–7). The cells were transfected using the calcium phosphate method at high cell density (Chen and Okayama, 1987, Mol. Cell. Biol. 7:2745–52). Eighteen hours after the addition of DNA precipitate, the cells were washed once and supplied with fresh medium containing 0.5% serum. Forty-eight hours after transfection, cells were split at least 1:10. Medium containing 1 μM insulin was added 12 hours later. Medium containing insulin was changed 3 times a day. Cells in culture were washed thoroughly with PBS each time the media was changed in order to remove detached cells.

The presence of insulin does not cause cell death, but detachment, so it is necessary to maintain the selective pressure of insulin presence until stable co-transfected clones have grown to sufficient numbers to be isolated and characterized. This process took approximately four weeks.

The antibodies to RPTPα and RPTPε were prepared by standard techniques in rabbits using peptide fragments derived from the C-terminus of RPTPα and RPTPε as immunogen. Analysis of protein expression and phosphorylation was performed as described in Section 6.1.

7.2. SELECTION AND ANALYSIS OF CELLS BY TRANSFECTION WITH cDNAS ENCODING PTPS

The specificity of each PTP for the insulin receptor was determined by assaying insulin-induced phenotypic changes in the cells and phosphorylation of insulin receptor β-subunit by Western Blot as described below.

7.2.1. INSULIN-INDUCED CHANGE IN PHENOTYPE

Figure 3A:
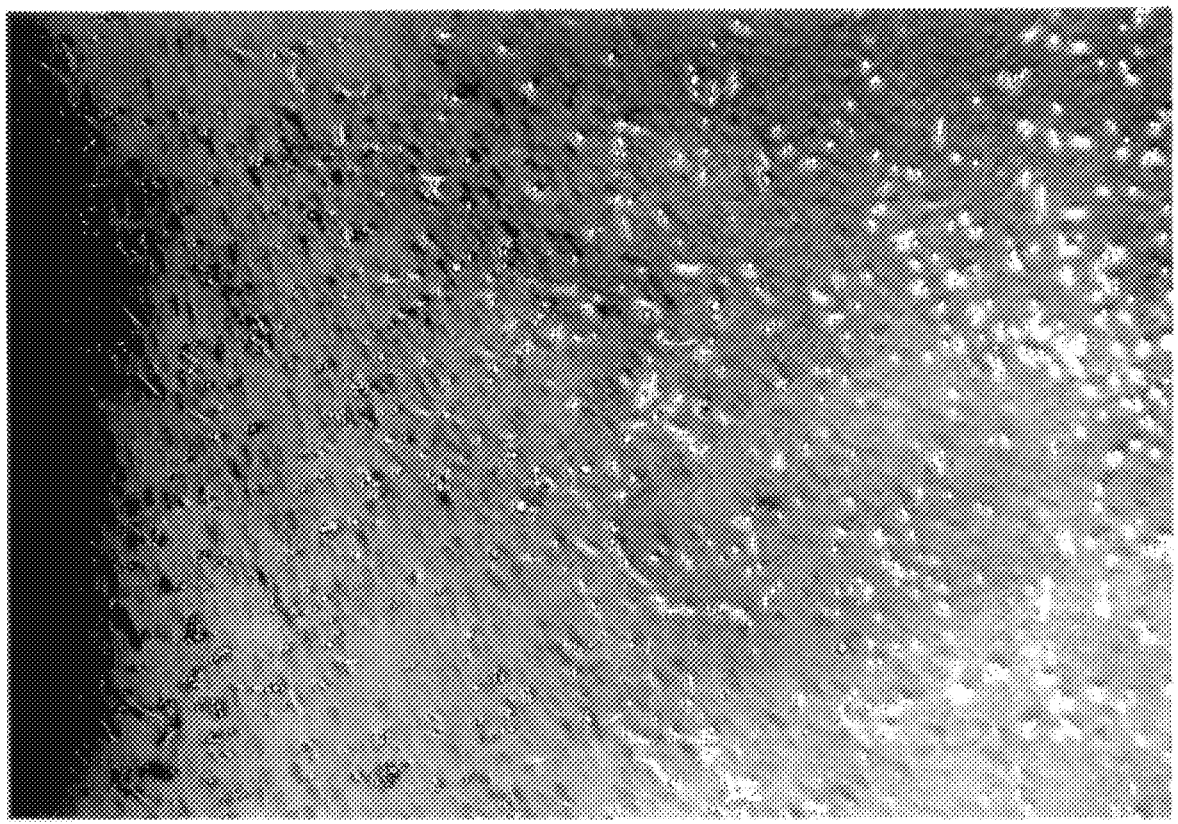
FIG. 3A is a photograph showing the insulin-induced change in phenotype of a BHK cell line expressing the insulin receptor.
Figure 3B:
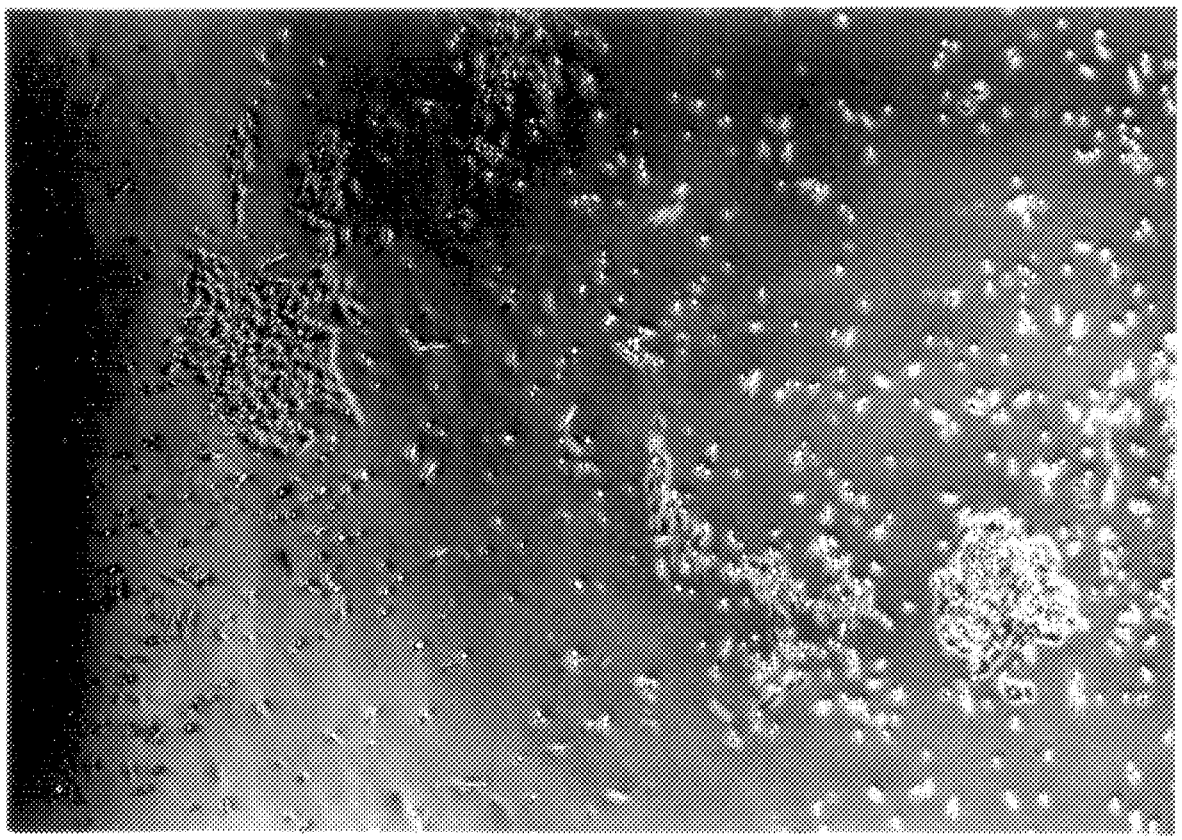
FIG. 3B is a photograph showing the phenotype of a BHK cell line coexpressing the insulin receptor and RPTPα in the presence of insulin.

In the presence of 1 μM insulin IR/BHK cells display an abnormal phenotype, i.e., rounding up and becoming detached from the plastic surface (FIG. 3A). The change in the phenotype induced by insulin was most pronounced at low cell density and in the presence of 10% fetal calf serum. IR/BHK cells were transfected with cDNAs coding for PTP1B, PTP1BΔ299, PTP1C, PTPμ, CD45, RPTPκ, RPTPα, RPTPε, LAR, and LAR(domain 1) to determine which of these PTPs were capable of modulating IR activity thereby preventing this morphological change of the cells. Only RPTPα and RPTPε, were able to restore the phenotype of the cells. These co-transfected cells exhibited the normal phenotype and did not respond in the same manner to high doses of insulin as the cells transfected with IR alone (FIG. 3B).

7.2.2. AUTOPHOSPHORYLATION ASSAY BY WESTERN BLOT

Two stably cotransfected clones for each cotransfection (IR+RPTPα and IR+RPTPε) were starved overnight in DMEM/high glucose containing 0% fetal calf serum then stimulated with 1 μM insulin for 10 minutes. The cells were lysed and the phosphotyrosine content of insulin receptor β-subunit was detected by Western blotting (FIGS. 4 and 5) using antiphosphotyrosine antibodies.

FIG. 4A shows the phosphorylation status of IR in stable BHK cell clones coexpressing IR and RPTPα. In control cells a strong tyrosine phosphorylation of insulin receptors β-subunit could be detected. This phosphorylation level was lower with the clones obtained after transfection with cDNA encoding RPTPα. FIG. 4B shows the level of RPTPα expression in the cotransfected clones. A band immunoreactive with anti-RPTPα antibodies could be detected in the cotransfected clones. FIG. 4C shows the level of IR expression in control and cotransfected clones which was similar.

As shown in FIG. 5A, 5B and 5C, the pattern of phosphorylation and expression levels in stable cell clones coexpressing IR and RPTPε are similar to that of IR and RPTPα. The data suggests that the restoration of normal phenotype of the cotransfected cells was associated with the dephosphorylation of the insulin receptor or downstream key signaling event.

In the presence of insulin, RPTPα and RPTPε modulates IR signal transduction and downstream cellular processes, which prevent changes in cell morphology and adhesion properties. These cell lines can be used in a drug screen whereby any biological effect of the test compound in vivo on insulin signal transduction may be monitored by changes in the cell morphology and adhesion properties or by phosphorylation state of the insulin receptor. Drugs that interfere with RPTPα or RPTPε activity would make the cells respond to insulin and re-exhibit the insulin-sensitive phenotype and receptor phosphorylation.

8. EXAMPLE: DIRECT INTERACTION BETWEEN IR AND RPTPα

This example shows the direct association between RPTPα and the insulin receptor. The example also demonstrates that dephosphorylation of IR by RPTPα and RPTPε results in a reduction of IR kinase activity.

8.1. MATERIALS AND METHODS

A BHK cell line overexpressing human insulin receptor (IR) was used as a source of the receptor. One 15-cm plate of confluent BHK cells was starved overnight in DMEM medium containing 0.5% FCS. The cells were lysed in 1 ml of lysis buffer (50 mM Hepes pH 7.5, 150 mM NaCl, 10% glycerin, 1% Triton X-100, vanadate 100 µM, protease inhibitors) and the lysate was spun down in a microfuge for 15 minutes at 13,000 rpm. One ml of the supernatant was incubated with 1 ml of wheat germ agglutinin sepharose beads for 4 hours at 4° C. with shaking. The beads were washed 5 times each with 2 ml HNTG (Hepes 20 mM pH 7.5, NaCl 150 mM, 0.1% Triton X-100, 10% glycerin) and once with 2 ml Hepes 20 mM, pH 7.5. The beads were then divided into three aliquots of 300 µl each. To aliquot 2 was added 228 µl Hepes pH 7.5 (20 mM), 39 µl MnCl$_2$ (150 mM), 27 µl ATP (10 mM), 6 µl insulin ($10^{-4}$M), 4 µl vanadate (40 mM). To aliquot 3, instead of ATP, 27 µl of ATPγS (10 mM) was added. To aliquot 1 27 µl of water was added, instead of ATP or ATPγS. ATPγS is a non-hydrolyzable form of ATP used in this experiment to see if stabilizing the conformation of the IR would affect its association with RPTPα. The aliquots of beads were incubated for 30 minutes at room temperature with shaking and then washed 5 times with HNTG (1 ml each). IR was eluted from the beads by adding 900 µl (3 times 300 µl) of 0.3M N-acetyl-glucosamine in HNTG. The eluates were stored frozen. Crude lysates of 293 cells transiently expressing RPTPα were used as a source of RPTPα. The cells were lysed as described above with the exception that the lysis buffer contained no vanadate. The antiphosphotyrosine phosphatase antibody 83-14 is described in section 6.1. For reprobing, blots were washed in 67 mM Tris-HCl (pH 6.8), 2% SDS, and 0.1% β-mercaptoethanol at 50° C. for 30 minutes.

8.2. COIMMUNOPRECIPITATION OF RPTPα WITH IR

Preparations of ATP-phosphorylated, ATP-γ-S-phosphorylated and non-phosphorylated IR were mixed with RPTPα and immunoprecipitated with an anti-IR monoclonal antibody 83-14. (Soos et al., Biochem J., 235:199–208, 1986) Including controls, six reactions of 200 µl each were set up as follows:

|  | 1 | 2 | 3 | 4 | 5 | 6 |
|---|---|---|---|---|---|---|
| Protein A-Sepharose (µl) | 40 | 40 | 40 | 40 | 40 | 40 |
| RPTPα (µl crude lysate) | — | 50 | 50 | 50 | 50 | 50 |
| IR (µl) | — | — | — | 70 | — | — |
| IR + ATP (µl) | — | — | — | — | 70 | — |
| IR + ATPγS (µl) | — | — | — | — | — | 70 |
| Lysis buffer (µl) | 50 | — | — | — | — | — |
| HNTG (µl) | 110 | 110 | 108 | 38 | 38 | 38 |
| 83-14 (µl) | — | — | 2 | 2 | 2 | 2 |

The reactions were incubated at 4° C. for 2 hours, washed four times each with 1 ml HNTG. Forty µl of 2× Laemmli buffer was added to the beads and 30 µl was analyzed by SDS-PAGE and transferred to a filter. The filter was reacted with a rabbit anti-RPTPα antibody at 1:1000 dilution. As indicated by FIG. 6A, using 83-14 to immuno-precipitate RPTPα was coimmunoprecipitated only with IR (lane 4) but not with the two phosphorylated receptors (lane 5 and 6). As a control, FIG. 6B showed the same filter reprobed with an anti-IR β chain antibody (104).

8.3. DEMONSTRATION OF ELUTION OF RPTPα FROM AUTOPHOSPHORYLATED IR

RPTPα and IR were coimmunoprecipitated using an anti-IR antibody. The reaction contained 250 µl protein A-Sepharose, 700 µl non-phosphorylated IR, 500 µl RPTPα, 20 µl antibody (83-14), 550 µl HNTG and were incubated at 4° C. for 2 hours. The beads were washed 4 times each with 1 ml HNTG and then divided into 9 aliquots of about 25 µl of beads each. IR autophosphorylation was allowed to proceed directly on the beads. To aliquot 1, 25 µl Laemmli buffer was added. To aliquots 2 and 6, 40 µl HNTG containing 5 mM EDTA and 1 mM ATP was added. To aliquots 3 and 7, 40 µl HNTG containing 5 mM EDTA, 1 mM ATP and $10^{-6}$M insulin was added. To aliquots 4 and 8, 40 mM HNTG containing 15 mM MgCl$_2$, 1 mM ATP and $10^{-6}$M insulin was added. Aliquots 2, 3, 4, and 5 and aliquots 6, 7, 8 and 9 were incubated for 15 and 30 mins respectively. The aliquots of beads were washed 3 times each with 1 ml HNTG, mixed with 25 µl of loading buffer and then analyzed by SDS-PAGE and Western blotting. The filter was reacted first with anti-RPTPα antibody, then an anti-phosphotyrosine antibody (5E2) (See Section 6.1) and finally an anti-IR antibody specific for the β chain (104). As shown in FIG. 7A, RPTPα that had been coimmunoprecipitated with IR was detected in the control reaction and in reactions containing a kinase inhibitor (EDTA). However, RPTPα was not detectable in lanes 5, 8 and 9 in which IR autophosphorylation is permitted. As shown in FIG. 7B, phosphotyrosine is present in the IR in lanes 4, 5, 8 and 9. FIG. 7C is a control showing the presence of immunoprecipitated IR in all the reactions. The data suggests that RPTPα was eluted from the IR when the receptor is autophosphorylated in vitro. 8.4. IN VITRO IR KINASE ACTIVITY ASSAY Equal numbers of BHK cells overexpressing IR plus RPTPα or RPTPε were grown in 6-well dishes and treated with $10^{-6}$-M insulin for 0, 2, 10, 30, 60 and 120 minutes. After treatment with insulin, 300 µl of lysis buffer as described in section 8.1 and in addition containing 5 mM EDTA and 5 mM vanadate, was added to each well. Ten µl of the cell lysates, prepared as in section 8.1, were immunoprecipitated by reacting for 2 hrs at 4° C. with 0.5 µl 83-14 antibody, 20 µl protein A-sepharose and 20 µl HNTG. The beads were washed 3 times each with 1 ml of HNTG and divided into 2 samples.

The kinase activity of the immunoprecipitated IR was measured as follows. A peptide corresponding to major autophosphorylation sites of IR (Novo) was used in accordance to the method described in J. Biol. Chem. 267:13811–14 with slight modifications. To each sample containing 10 µl of beads was added 15 µl of water and 25 µl of a phosphorylation mixture which contained 100 mM Hepes, pH 7.5, 0.2% Triton X-100, 10 mM MnCl$_2$, 20 mM MgCl$_2$, 1.2 mM peptide, 10 µM ATP, and 0.1 µCi γ$^{32}$P ATP. The kinase reaction was allowed to proceed for 15 minutes at 25° C. and was stopped by adding 50 µl of 10% TCA. The mixture was centrifuged to pellet the beads and 60 µl of the supernatant was spotted on a piece of 3 cm×3 cm phosphocellulose paper. The paper was dried, washed 5 times in 0.85% phosphoric acid and the radioactivity on the paper was measured by a counter using the $^3$H channel.

In FIG. 8, the amount of radioactivity detected was plotted against incubation time in the presence of insulin.

Each point represents the result of two independent determinations. This assay detects kinase enzymatic activity and is, therefore, a more sensitive method for showing the modulatory activity of RPTPα and RPTPε on the insulin receptor. Phosphorylation is possible on several tyrosine residues whereas removal of only one phosphate may abrogate kinase activity. In order to ensure that the same amount of IR was present in each sample, IR bound to the beads was checked in parallel by Western blotting using anti-IR antibodies as described in the previous examples.

9. EXAMPLE: SCREENING ASSAY FOR INHIBITORS OF INSULIN RECEPTOR-RELATED PHOSPHATASE ACTIVITY

This example describes a screening assay for determining the potential of an exogenously applied test substance in modulating the activity of insulin receptor-related phosphatases in a target cell. In this assay, cells expressing both the IR and IR-modulating phosphatases were exposed to a test substance in the presence or absence of insulin. The phosphorylation level of the insulin receptor in the cells were assessed by an immunoassay based on an antiphosphotyrosine antibody. The phosphatase inhibitory activity of a test substance was detected by an increase in the level of IR phosphorylation relative to the control.

NIH3T3 cells transfected with the gene expressing the human IR were suspended in DMEM medium (Dulbecco's modified Eagle's medium, with 10% calf serum). The cells were centrifuged once at 1500 rpm for 5 minutes, resuspended in seeding medium (DMEM, 0.5% calf serum) and then counted with trypan blue to assess viability (90% or above is acceptable). The cells in DMEM medium were seeded in 96 well microtitre plates at a density of about 25,000 cells per well in a volume of 100 µl, and incubated in 5% $CO_2$ at 37° C. for about 20 hours. Test compound dissolved in a vehicle such as dimethyl sulphoxide, PBS or water was added to the culture at a concentration ranging from 10 µM to 100 µM, and 10 µl was added to each well to a final concentration of 1–10 µM. Control samples received the vehicle alone. The cells were incubated at 37° C. in 5% $CO_2$ for 30 to 120 minutes. Cell lysate was prepared by removing the media, and lysing the cells on ice for 5 minutes with 100 µl of HNTG buffer (HNTG buffer contains 1× HNTG, 5 mM EDTA, 5 mM $Na_3VO_4$, 2 mM sodium phosphate 5× HNTG is 20 mM HEPES, 150 mM NaCl, 10% glycerol, 0.2% Triton x-100).

The immunoassay was based on a polyclonal rabbit antiphosphotyramine antibody which was prepared according to Harlow and Lane, Antibodies, Cold Spring Harbor Laboratory, (1988) using phosphotyramine coupled to keyhole limpet hemocyanin as an immunogen. The immunoassay was carried out in 96-well microtitre plates coated with an anti-IR monoclonal antibody (18-34) to capture the IR in the cell lysate.

The coated microtitre plates were prepared by incubating the wells each with 100 µl of coating buffer containing 0.5 µg of the 18-34 antibody at room temperature for 2 hours. The coating buffer was then removed and replaced with 200 µl blocking buffer (5% dry milk in PBS) which was incubated shaking for 30 minutes at room temperature. The plates were then washed four times with TBST buffer (150 mM NaCl, 50 mM Tris-HCl pH 7.2, 0.1% Triton x-100) prior to use.

Samples of cell lysates were added to the coated wells and incubated shaking at room temperature for 1 hour. The lysates were then removed from the wells which were washed four times with TBST buffer. The antiphosphotyrosine antibody diluted 1:3000 in TBST (100 µl) was applied and incubated, shaking at room temperature. After thirty minutes of incubation, the antibody was removed and the wells were washed four times with TBST. A peroxidase-conjugated anti-rabbit IgG (100 µl, TAGO, Burlingame, Calif.) diluted 1:3000 in TBST was added to the wells and incubated for another 30 minutes at room temperature. The anti-rabbit IgG antibody was then removed and the wells were washed 4 times with TBST. A 100 µl, solution of a calorimetric substrate (10 ml ABTS (Sigma) in 100 mM citric acid, 250 mM $Na_2HPO_4$, pH4.0 and 1.2 µ$H_2O_2$) was added and incubated at room temperature for 20 minutes. The absorbance at 410 nm was then determined for each sample.

The screening assay system may be used to identify and evaluate, for example, the following compound as a PTP inhibitor which may be used in accordance with the invention.

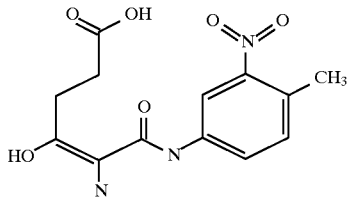

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of modulating signal transduction mediated by an insulin receptor type tyrosine kinase in a cell comprising administering to the cell an organic compound that is not a vanadate, pervanadate, or a peptide, and that inhibits dephosphorylation of the insulin receptor type tyrosine kinase by a receptor protein phosphotyrosine phosphatase.

2. The method of claim 1 in which signal transduction is stimulated.

3. The method of claim 1 in which signal transduction is stimulated in the absence of ligand binding to the insulin receptor type tyrosine kinase.

4. The method of claim 1 in which the insulin receptor type tyrosine kinase is human insulin receptor tyrosine kinase.

5. The method of claim 4 in which signal transduction is stimulated.

6. The method of claim 4 in which signal transduction is stimulated in the absence of ligand binding to the insulin receptor type tyrosine kinase.

7. The method of claim 2, 3, 5 or 6 in which the PTP is human RPTPα.

8. The method of claim 2, 3, 5 or 6 in which the PTP is human RPTPε.

9. A method for modulating signal transduction mediated by an insulin receptor type tyrosine kinase in a subject comprising administering to the subject an organic compound that is not a vanadate, pervanadate, or a peptide, and that prolongs or enhances phosphorylation of the insulin receptor type tyrosine kinase.

10. The method of claim 9 in which signal transduction is stimulated.

11. The method of claim 9 in which signal transduction is stimulated in the absence of ligand binding to the insulin receptor type tyrosine kinase.

12. The method of claim 9 in which the insulin receptor type tyrosine kinase is insulin receptor.

13. The method of claim 12 in which the subject has type I or type II diabetes mellitus.

14. A method of modulating signal transduction mediated by an insulin receptor type tyrosine kinase in a cell comprising administering to the cell an organic compound that is not a peptide, wherein said organic compound specifically inhibits dephosphorylation of the insulin receptor type tyrosine kinase by a receptor protein phosphotyrosine phosphatase.

15. The method of claim 14 in which signal transduction is stimulated.

16. The method of claim 14 in which signal transduction is stimulated in the absence of ligand binding to the insulin receptor type tyrosine kinase.

17. The method of claim 14 in which the insulin receptor type tyrosine kinase is human insulin receptor tyrosine kinase.

18. The method of claim 14 in which the receptor protein phosphotyrosine phosphatase is human RPTPα.

19. The method of claim 14 in which the receptor protein phosphotyrosine phosphatase is human RPTPε.

20. A method for modulating signal transduction mediated by an insulin receptor type tyrosine kinase in a subject comprising administering to the subject an organic compound that is not a peptide, wherein said organic compound specifically prolongs or enhances phosphorylation of the insulin receptor type tyrosine kinase.

21. The method of claim 20 in which signal transduction is stimulated.

22. The method of claim 20 in which signal transduction is stimulated in the absence of ligand binding to the insulin receptor type tyrosine kinase.

23. The method of claim 20 in which the insulin receptor type tyrosine kinase is insulin receptor.

24. The method of claim 23 in which the subject has type I or type II diabetes mellitus.

25. A method of modulating signal transduction mediated by an insulin receptor type tyrosine kinase in a cell comprising administering to the cell an organic compound that is not a vanadate, pervanadate, or a peptide, and that inhibits dephosphorylation of the insulin receptor type tyrosine kinase by a receptor protein phosphotyrosine phosphatase α.

26. A method of modulating signal transduction mediated by an insulin receptor type tyrosine kinase in a cell comprising administering to the cell an organic compound that is not a peptide wherein said organic compound specifically inhibits dephosphorylation of the insulin receptor type tyrosine kinase by a receptor protein phosphotyrosine phosphatase α.

* * * * *